(12) United States Patent
Erekovcanski et al.

(10) Patent No.: US 11,273,298 B2
(45) Date of Patent: Mar. 15, 2022

(54) UNIVERSAL SINGLE-USE CAP FOR MALE AND FEMALE CONNECTORS

(71) Applicant: Becton, Dickinson and Company, Franklin Lakes, NJ (US)

(72) Inventors: Nicholas Erekovcanski, Butler, NJ (US); Chang Jiang, Butler, NJ (US); Paul Marici, Piscataway, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/378,015

(22) Filed: Apr. 8, 2019

(65) Prior Publication Data

US 2019/0308006 A1    Oct. 10, 2019

Related U.S. Application Data

(60) Provisional application No. 62/655,489, filed on Apr. 10, 2018.

(51) Int. Cl.
 *A61M 39/16* (2006.01)
 *A61M 39/20* (2006.01)
 *A61M 39/10* (2006.01)

(52) U.S. Cl.
 CPC .......... *A61M 39/162* (2013.01); *A61M 39/20* (2013.01); *A61M 2039/1083* (2013.01); *A61M 2039/1088* (2013.01)

(58) Field of Classification Search
 CPC .. A61M 39/16; A61M 39/162; A61M 39/165; A61M 2039/1083; A61M 2039/1088; A61M 39/20; A61M 2039/1027; A61M 2039/1033; A61M 2039/1038; A61M 2039/1077
 See application file for complete search history.

(56) References Cited

U.S. PATENT DOCUMENTS

| | | | |
|---|---|---|---|
| 3,403,679 | A | 10/1968 | Sinclair et al. |
| 4,417,890 | A | 11/1983 | Dennehey et al. |
| 4,597,758 | A | 7/1986 | Aalto et al. |

(Continued)

FOREIGN PATENT DOCUMENTS

| | | |
|---|---|---|
| CN | 204161736 U | 2/2015 |
| DE | 20017013 U1 | 12/2000 |

(Continued)

OTHER PUBLICATIONS

PCT International Search Report and Written Opinion in PCT/US2019/026482 dated Jul. 30, 2019, 13 pages.

(Continued)

*Primary Examiner* — Amber R Stiles
*Assistant Examiner* — Avery Smale
(74) *Attorney, Agent, or Firm* — Servilla Whitney LLC

(57) ABSTRACT

A device for connection to a medical connector, the device includes an outer cap, an inner cap and a peelable seal. The outer cap configured to define a chamber to contain an absorbent material and disinfectant or antimicrobial agent. The outer cap including one or more threads adapted to engage with a female luer connector. The inner cap including one or more thread-tabs adapted to engage a male luer connector. The peelable seal prevents the disinfectant or the antimicrobial agent from exiting the chamber.

14 Claims, 25 Drawing Sheets

(56) References Cited

U.S. PATENT DOCUMENTS

| | | |
|---|---|---|
| 4,642,102 A | 2/1987 | Ohmori |
| 4,711,363 A | 12/1987 | Marino |
| 4,738,376 A | 4/1988 | Markus |
| 4,906,231 A | 3/1990 | Young |
| 5,084,017 A | 1/1992 | Maffetone |
| 5,496,288 A | 3/1996 | Sweeny |
| 5,676,406 A | 10/1997 | Simmons et al. |
| 5,755,696 A | 5/1998 | Caizza |
| 6,632,199 B1 | 10/2003 | Tucker et al. |
| 7,083,605 B2 | 8/2006 | Miyahara |
| 8,012,131 B2 | 9/2011 | Moser et al. |
| 8,388,894 B2 | 3/2013 | Colantonio |
| 8,647,308 B2 | 2/2014 | Solomon et al. |
| 8,721,627 B2 | 5/2014 | Alpert et al. |
| 8,777,504 B2 | 7/2014 | Shaw et al. |
| 8,784,388 B2 | 7/2014 | Charles et al. |
| 8,961,475 B2 | 2/2015 | Solomon et al. |
| 9,039,989 B2 | 5/2015 | Liu et al. |
| 9,192,449 B2 | 11/2015 | Kerr et al. |
| 10,099,048 B2 | 10/2018 | Chiu et al. |
| 10,166,381 B2 | 1/2019 | Gardner et al. |
| 10,589,080 B2 | 3/2020 | Hitchcock et al. |
| 10,603,481 B2 | 3/2020 | Avula et al. |
| 2003/0209681 A1 | 11/2003 | Leinsing et al. |
| 2004/0039341 A1 | 2/2004 | Ranalletta |
| 2005/0147525 A1 | 7/2005 | Bousquet |
| 2007/0060904 A1 | 3/2007 | Vedrine et al. |
| 2008/0171995 A1 | 7/2008 | Vitullo et al. |
| 2008/0177250 A1 | 7/2008 | Howlett et al. |
| 2010/0004020 A1 | 1/2010 | Shaw et al. |
| 2010/0049170 A1 | 2/2010 | Solomon et al. |
| 2010/0050351 A1 | 3/2010 | Colantonio et al. |
| 2010/0100056 A1* | 4/2010 | Cawthon ............. A61M 39/165 604/256 |
| 2011/0046603 A1 | 2/2011 | Felsovalyi et al. |
| 2011/0054440 A1 | 3/2011 | Lewis |
| 2011/0264037 A1 | 10/2011 | Foshee et al. |
| 2012/0039764 A1 | 2/2012 | Solomon et al. |
| 2012/0123386 A1 | 5/2012 | Tsals |
| 2012/0302997 A1 | 11/2012 | Gardner et al. |
| 2013/0033864 A1 | 2/2013 | Spinger et al. |
| 2013/0085474 A1 | 4/2013 | Charles et al. |
| 2013/0171030 A1 | 7/2013 | Ferlic et al. |
| 2013/0197485 A1* | 8/2013 | Gardner ............. A61M 39/162 604/533 |
| 2014/0052074 A1 | 2/2014 | Tekeste |
| 2014/0150832 A1 | 6/2014 | Rogers et al. |
| 2015/0094666 A1 | 4/2015 | Bates et al. |
| 2015/0374968 A1 | 12/2015 | Solomon et al. |
| 2016/0045629 A1 | 2/2016 | Gardner et al. |
| 2017/0203092 A1 | 7/2017 | Ryan et al. |
| 2018/0200145 A1 | 7/2018 | Sanders et al. |
| 2018/0200500 A1 | 7/2018 | Ziebol et al. |
| 2018/0256879 A1 | 9/2018 | Chiu et al. |
| 2018/0256883 A1* | 9/2018 | Follman ................ A61M 39/20 |
| 2019/0151643 A1 | 5/2019 | Alpert |
| 2019/0234540 A1 | 8/2019 | Marici et al. |
| 2019/0308006 A1 | 10/2019 | Erekovcanski et al. |
| 2019/0351212 A1 | 11/2019 | Dudar et al. |
| 2021/0187267 A1 | 6/2021 | Jiang |

FOREIGN PATENT DOCUMENTS

| | | |
|---|---|---|
| DE | 10247963 A1 | 5/2004 |
| EP | 2606930 A1 | 6/2013 |
| EP | 2832391 B1 | 2/2015 |
| EP | 3275490 A1 | 1/2018 |
| GB | 2408259 A | 5/2005 |
| GB | 2518646 A | 4/2015 |
| WO | 200024442 A1 | 5/2000 |
| WO | 200224551 A1 | 3/2002 |
| WO | 2011066586 A1 | 6/2011 |
| WO | 2014159346 A1 | 10/2014 |
| WO | 2015127285 A1 | 8/2015 |
| WO | 2017087400 A1 | 5/2017 |
| WO | 2017095373 A1 | 6/2017 |
| WO | 2018106508 A1 | 6/2018 |
| WO | 2019152482 A1 | 8/2019 |
| WO | 2019212637 A1 | 11/2019 |
| WO | 2020112767 A1 | 6/2020 |

OTHER PUBLICATIONS

Non-Final Office Action in U.S. Appl. No. 15/838,461 dated Jul. 24, 2020, 10 pages.
Non-Final Office Action in U.S. Appl. No. 16/253,683, dated Jun. 26, 2020, 9 pages.
Non-Final Office Action in U.S. Appl. No. 16/254,747, dated Aug. 20, 2020, 14 pages.
PCT International Search Report and Written Opinion in PCT/US2020/015535 dated May 4, 2020, 13 pages.
PCT International Search Report and Written Opinion in PCT/US2020/041097 dated Oct. 27, 2020, 18 pages.
Final Office Action in U.S. Appl. No. 16/253,683, dated Dec. 23, 2020, 9 pages.
Final Office Action in U.S. Appl. No. 16/254,747, dated Jan. 22, 2021, 15 pages.
PCT International Search Report and Written Opinion in PCT/US2020/057611 dated Feb. 5, 2021, 11 pages.
PCT International Search Report and Written Opinion in PCT/US2020/041312 dated Oct. 19, 2020, 11 pages.
PCT International Search Report and Written Opinion in PCT/US2020/044942 dated Oct. 16, 2020, 15 pages.
PCT International Search Report and Written Opinion in PCT/US2020/044951 dated Oct. 14, 2020, 14 pages.
PCT International Search Report and Written Opinion in PCT/US2021/027214 dated Jul. 19, 2021, 14 pages.
PCT International Search Report and Written Opinion in PCT/US2021/027218 dated Jul. 22, 2021, 14 pages.
PCT International Search Report and Written Opinion in PCT/US2021/027220 dated Jul. 21, 2021, 15 pages.
PCT Invitation to Pay Additional Fees in PCT/US2021/027219, dated Jul. 22, 2021, 15 pages.
PCT International Search Report and Written Opinion in PCT/US2020/065229 dated Mar. 29, 2021, 12 pages.
PCT Invitation to Pay Additional Fees in PCT/US2021/019546, dated Jun. 15, 2021, 17 pages.
International Search Report in PCT/US2019/015789, dated Apr. 16, 2019, 12 pages.
PCT International Search Report and Written Opinion in PCT/US2021/027219 dated Oct. 22, 2021, 22 pages.

* cited by examiner

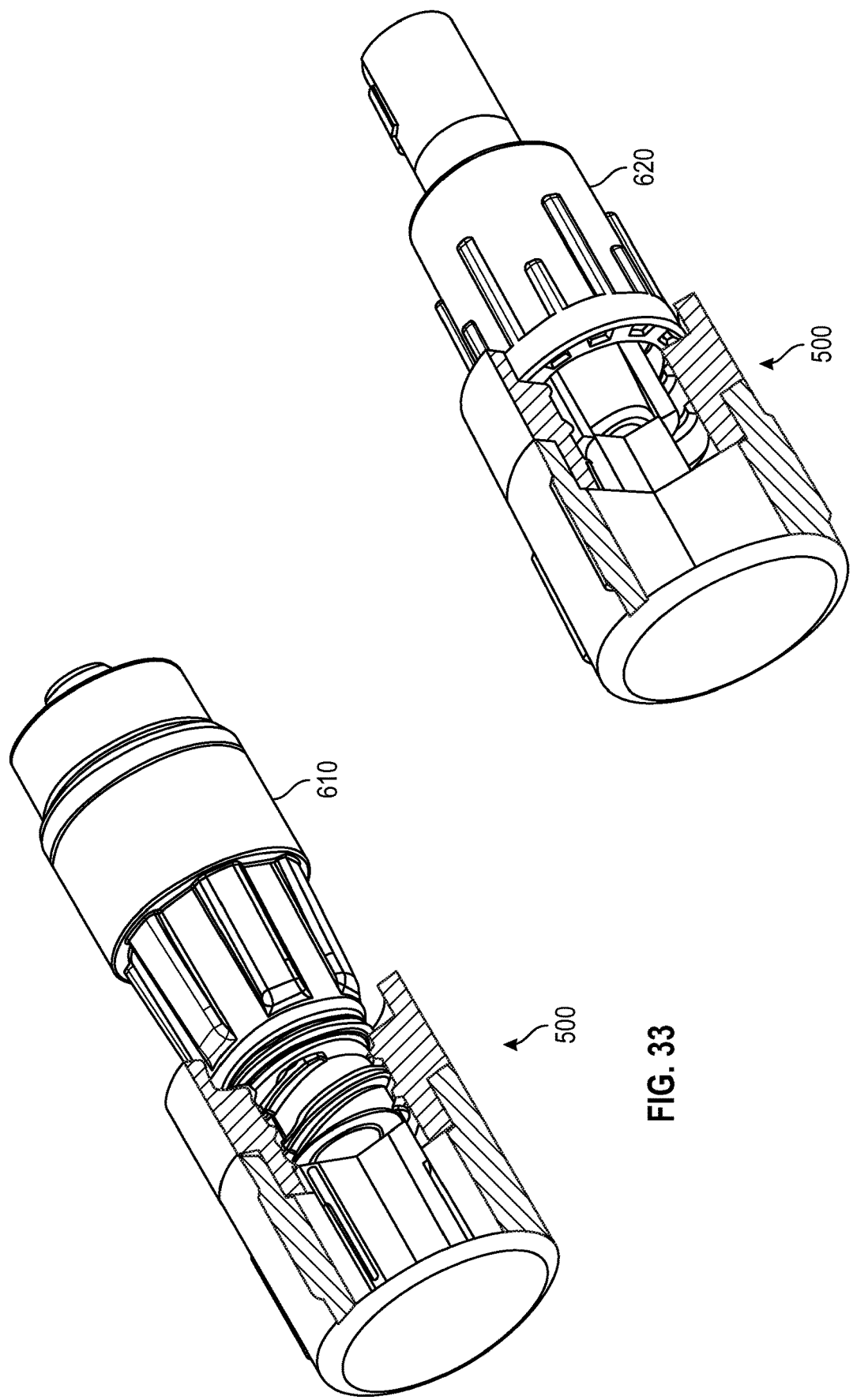

UNIVERSAL SINGLE-USE CAP FOR MALE AND FEMALE CONNECTORS

CROSS-REFERENCE TO RELATED APPLICATIONS

This application claims priority under 35 U.S.C. § 119(e) to U.S. Provisional Application No. 62/655,489, filed Apr. 10, 2018, the disclosures of which are incorporated herein by reference in their entirety.

TECHNICAL FIELD

The present disclosure generally relates to a device for disinfecting and sterilizing access ports with, e.g., male and female luer fitting, and, in particular, to disinfecting and sterilizing devices capable of accommodating multiple types of connectors.

BACKGROUND

Vascular access devices (VAD's) are commonly used therapeutic devices and include intravenous (IV) catheters. There are two general classifications of VAD's, peripheral catheters and central venous catheters. Bacteria and other microorganisms may gain entry into a patient's vascular system from access hubs and ports/valves upon connection to the VAD to deliver the fluid or pharmaceutical. Each access hub (or port/valve or connection) is associated with some risk of transmitting a catheter related bloodstream infection (CRBSI), which can be costly and potentially lethal.

In order to decrease catheter-related bloodstream infection (CRBSI) cases and to ensure VAD's are used and maintained correctly, standards of practice have been developed, which include disinfecting and cleaning procedures.

Disinfection caps have been added to the Society for Healthcare Epidemiology of America (SHEA) guidelines and early indications are that caps will also be incorporated into the 2016 Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including the CRBSI events described before. Nurses will typically utilize a 70% IPA alcohol pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Currently, caps for male needleless connectors, female needleless connectors, intravenous (IV), and hemodialysis lines use different designs and are therefore limited to the types of connectors to which the cap can be attached. Prior disinfecting caps were designed to fit one type of connector only, and were specific to one particular size and/or shape of connector. Thus, there is a need for a disinfecting device capable of accommodating multiple types of connectors to streamline the disinfecting process. There is also a need for a disinfecting device capable of continuous disinfection for multiple days.

SUMMARY

One aspect of the present disclosure pertains to a device for connection to a medical connector. The device, according to a first exemplary embodiment of the present disclosure, generally comprises an outer cap, an inner cap, and a peelable seal. In one or more embodiments, the outer cap comprises an integral body, a closed end, and an annular wall having a length extending from the closed end to an open end defining a chamber. The chamber may contain an absorbent material and disinfectant or antimicrobial agent. The open end of the outer cap defines an end face. The annular wall of the outer cap includes an outer cap exterior wall surface and an outer cap interior wall surface. The interior wall surface includes one or more threads. The inner cap includes an integral body having an annular wall having an exterior wall surface and an interior wall surface with a first end of the inner cap facing the closed end of the outer cap, a second end of the inner cap facing the open end of the outer cap. The exterior wall surface of the first end of the inner cap includes one or more threads which may engage with the threads on the interior wall surface of the outer cap. The exterior wall surface of the second end of the inner cap includes one or more threads adapted to engage a male luer connector. When the threads of the inner cap are engaged with a male luer connector, the threads of the outer cap will be passive. Alternatively, when the threads of the outer cap are engaged with a female luer connector, the threads of the inner cap will be passive. In one or embodiments, the peelable seal may be placed on the end face to prevent the disinfectant or the antimicrobial agent from exiting the chamber.

When the device is removed from its packaging, the open end of the outer cap is situated on a same horizontal plane as the second end of the inner cap in an initial state. To connect the device to a male luer connector, the user applies an axial load such that a male luer connector is engaged to the one or more threads of the exterior wall surface of the second end of the inner cap and rotated in a clockwise direction, the inner cap partially protrude out from the open end of the outer cap. When the inner cap partially protrudes out from the open end of the outer cap, there is no space that exists between the device and the connector. When a male luer connector is engaged to the one or more threads of the exterior wall surface of the second end of the inner cap and rotated in a counter-clockwise direction, the inner cap retracts into the chamber of the outer cap. When a female luer connector is engaged to the device, the inner cap slips and retracts into the chamber of the outer cap. Once the device is engaged to the connector, the device may be removed from the connector by rotating the device counter-clockwise. Upon disengagement, the inner cap and the outer cap remain intact and attached to each other.

The device is designed to be compatible in interacting with various disinfectants. In one or more embodiments, the disinfectant or antimicrobial agent may include variations of alcohol or chlorhexidine. The disinfectant or antimicrobial agent can be a fluid or a gel selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

In one or more embodiments, the outer cap exterior wall surface includes a plurality of grip members.

In one or more embodiments, the female connector may be a needle-free connector, stopcock, or hemodialysis connector. In one or more embodiments, the male connector may be an intravenous tubing end or stopcock.

Another aspect of the present disclosure pertains to a device for connection to a medical connector according to a second exemplary embodiment of the present disclosure generally comprises an outer cap, an inner cap, and a peelable seal.

The outer cap comprises a body, a closed end, an annular wall having a length extending from the closed end to an open end and defining a chamber containing an absorbent material and disinfectant or antimicrobial agent. The open end defines an end face. Annular wall of the outer cap includes an outer cap exterior wall surface and an outer cap interior wall surface. The outer cap interior wall surface comprises one or more grooves and one or more threads adapted to engage with a female luer connector. In one or more embodiments, the female connectors may be in the form of needle-free connectors, stopcocks, and hemodialysis connectors. In one or more alternate embodiments, the body of the outer cap may be comprised of two components, where a rear-end component with an inner cavity is screwed onto the front-end component of the cap body via threads or welding.

The inner cap comprises a body having an annular wall having an exterior wall surface and an interior wall surface with a first end of the inner cap facing the closed end of the outer cap. A second end of the inner cap faces the open end of the outer cap. The outer cap interior wall surface comprises one or more grooves along which the inner cap is able to slide. The exterior wall surface of the first end of the inner cap includes two shaft-like wings to fit into the one or more grooves of the outer cap interior wall surface to facilitate the slide motion without allowing signification relative rotation between the inner cap with respect to the outer cap. The outer-most diameter of the threads of the inner cap is designed to have minimum interference, e.g. sliding fit or strip fit, with the threads of the outer cap to allow relative linear motion and also facilitate assembly of device. The teeth depth of the threads of the inner cap and the outer cap is desired to be sufficient to engage with the male and female luer connectors. The exterior wall surface of the second end of the inner cap includes one or more thread-tabs adapted to engage a male luer connector. In one or more embodiments, the exterior wall surface of the second end of the inner cap includes two thread-tabs adapted to engage a male luer connector. The male luer connectors include collars with female threads. In one or more embodiments, the male connector can be an intravenous (I.V.) tubing end, stopcock or male lock luer.

Inner cap can slide back and forth with respect to outer cap. In one or more embodiments, the open end of the outer cap is situated on a same horizontal plane as the second end of the inner cap in an initial state. When a male luer connector is engaged to the one or more threads of the exterior wall surface of the second end of the inner cap, the inner cap slides against the outer cap to partially protrude out from the open end of the outer cap. When a female luer connector is engaged to the device, the inner cap slides against the outer cap and retracts into the chamber of the outer cap to allow the female luer connector to engage the one or more threads on the interior wall surface of the outer cap.

Disinfecting caps currently on the market are capable of only disinfecting one of the three types of luer fitting, namely female luer of needle-free connectors, female luer of stopcocks, and male luer connectors on intravenous injection sites. Thus, to avoid having to use different types of disinfecting caps to clean different types of connectors, the device is self-adaptive to different types of luer connectors due to the sliding mechanism between the inner cap that engages with male luer connectors and the outer cap that engages with female luer connectors, thereby allowing the user to clean different types of connectors with a single device. Upon mounting the outer cap onto female luer connectors, the inner cap retreats towards the chamber at the closed end of the outer cap, thus, providing space for female luer connectors to be inserted and screwed onto the threads of the outer cap. Upon mounting the inner cap of device onto a male luer connector, the one or more thread-tabs on the exterior wall surface of the second end of the inner cap engage with the threads on the male luer connector. Hence, the disclosed cap can be mounted onto both male and female luers.

The device can achieve disinfection when used on luer connectors by integrating disinfectant or antimicrobial agent in the chamber of the outer cap. The disinfectant or antimicrobial agent can be directly included in the chamber or disinfectant or antimicrobial agent can be absorbed into sponges or foam material that fills the chamber of outer cap. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

The peelable seal on the end face is to prevent the disinfectant or the antimicrobial agent from exiting the chamber.

In one or more embodiments, the outer cap exterior wall surface includes a plurality of grip members.

The outer-most diameter of the one or more thread-tabs of the inner cap has a minimum interference with the threads of the outer cap to allow for relative linear motion.

Another aspect of the present disclosure pertains to a device for connection to a medical connector according to a third exemplary embodiment of the present disclosure generally comprises an outer cap, an inner cap, and a peelable seal.

The outer cap comprises an integral body, a closed end, an annular wall having a length extending from the closed end to an open end and defining a chamber containing an absorbent material and disinfectant or antimicrobial agent. The open end defines an end face.

The annular wall of the outer cap comprises an outer cap exterior wall surface and an outer cap interior wall surface. The outer cap interior wall surface includes one or more grooves and one or more threads adapted to engage with a female luer connector, wherein at least a portion of said one or more threads on the outer cap interior wall surface comprise a gap that does not engage a mating feature of the inner cap.

The inner cap slidably engages with the outer cap. The inner cap comprises an integral body having an annular wall having an exterior wall surface and an interior wall surface with a first end of the inner cap facing the closed end of the outer cap and a second end of the inner cap facing the open end of the outer cap. The exterior wall surface of the first end of the inner cap includes two shaft-like wings to fit into the one or more grooves of the outer cap interior wall surface and facilitate the slide motion without allowing signification relative rotation between the inner cap with respect to the outer cap. The exterior wall surface of the second end of the inner cap includes one or more thread-tabs adapted to engage a male luer connector. The inner cap is in a slidable arrangement with the outer cap.

The peelable seal on the end face to prevent the disinfectant or the antimicrobial agent from exiting the chamber.

In one or more embodiments, the open end of the outer cap is situated on a same horizontal plane as the second end of the inner cap in an initial state.

When a male luer connector is engaged to the one or more threads of the exterior wall surface of the second end of the inner cap and rotated in a clockwise direction, the inner cap partially protrudes out from the open end of the outer cap.

When a male luer connector is engaged to the one or more threads of the exterior wall surface of the second end of the inner cap and rotated in a counter-clockwise direction, the inner cap retracts into the chamber of the outer cap.

When a female luer connector is engaged to the device, the inner cap slides against the outer cap and retracts into the chamber of the outer cap to allow the female luer connector to engage the one or more threads on the interior wall surface of the outer cap.

In one or more embodiments, the exterior wall surface of the second end of the inner cap includes two thread-tabs adapted to engage a male luer connector having collars with female threads.

In one or more embodiments, the outer cap exterior wall surface includes a plurality of grip members.

In one or more embodiments, the female connector may be selected from the group consisting essentially of needle-free connectors, catheter luer connectors, stopcocks, and hemodialysis connectors.

In one or more embodiments, the male connector may be an intravenous tubing end, stopcock or male lock luer.

In one or more embodiments, the threads of the inner cap and the threads of the outer cap are void of interference to enable a sliding fit.

In one or more embodiments, the gaps of the one or more threads of the outer cap interior wall surface are disposed adjacent to the grooves of the outer cap interior wall surface to allow sliding of the inner cap against the outer cap.

The gaps of the one or more threads of the outer cap interior wall surface accommodate the one or more thread-tabs on the exterior wall surface of the second end of the inner cap when the inner cap slides against the outer cap.

In one or more embodiments, the two shaft-like wings on the exterior wall surface of the first end of the inner cap further comprise one or more pockets having a snap-fit arrangement with one or more protrusions disposed on the one or more grooves of the outer cap interior wall surface to fix the position of the inner cap with the outer cap.

When a male luer connector is engaged to the one or more threads of the exterior wall surface of the second end of the inner cap and rotated in a clockwise direction, the one or more pockets on the two shaft-like wings of the inner cap disengage from the one or more protrusions on the outer cap interior wall surface to allow the inner cap to partially protrude out from the opening end of the outer cap.

When a female luer connector is engaged to the device, the inner cap will be pushed and the one or more pockets on the two shaft-like wings of the inner cap disengage from the one or more protrusions on the outer cap interior wall surface to allow the inner cap to move toward the closed end of the chamber.

In one or more embodiments, the two shaft-like wings on the exterior wall surface of the first end of the inner cap further comprise one or more protrusions having a snap-fit arrangement with one or more corresponding one or more pockets disposed on the one or more grooves of the outer cap interior wall surface to fix the position of the inner cap with the outer cap.

When a male luer connector is engaged to the one or more threads of the exterior wall surface of the second end of the inner cap and rotated in a clockwise direction, the one or more pockets on the two shaft-like wings of the inner cap disengages from the one or more protrusions on the outer cap interior wall surface to allow the inner cap to partially protrude out from the opening end of the outer cap.

When a female luer connector is engaged to the device, the inner cap will be pushed and the one or more pockets on the two shaft-like wings of the inner cap disengage from the one or more protrusions on the outer cap interior wall surface to allow the inner cap to move toward the closed end of the chamber.

Inner cap can slide back and forth with respect to outer cap. In one or more embodiments, the open end of the outer cap is situated on a same horizontal plane as the second end of the inner cap in an initial state. When a male luer connector is engaged to the one or more threads of the exterior wall surface of the second end of the inner cap, the inner cap slides against the outer cap to partially protrude out from the open end of the outer cap. When a female luer connector is engaged to the device, the inner cap slides against the outer cap and retracts into the chamber of the outer cap to allow the female luer connector to engage the one or more threads on the interior wall surface of the outer cap. The threads of the inner cap and the threads of the outer cap are intrinsically non-interfering with each other, and are no longer restrained by interference that enables sliding fit.

Disinfecting caps currently on the market are capable of only disinfecting one of the three types of luer fitting, namely female luer of needle-free connectors, female luer of stopcocks, and male luer connectors on intravenous injection sites. Thus, to avoid having to use different types of disinfecting caps to clean different types of connectors, device is self-adaptive to different types of luer connectors due to the sliding mechanism between the inner cap that engages with male luer connectors and the outer cap that engages with female luer connectors thereby allowing the user to clean different types of connectors with a single device. Thus, to avoid having to use different types of disinfecting caps to clean different types of connectors, device and other embodiments of the present disclosure provides a single device to be used for cleaning different types of connectors. Upon mounting the outer cap onto female luer connectors, the inner cap retreats towards the chamber at the closed end of the outer cap, thus, providing space for female luer connectors to be inserted and screwed onto the threads of the outer cap. Upon mounting the inner cap of device onto a male luer connector, the one or more thread-tabs on the exterior wall surface of the second end of the inner cap engage with the threads on the male luer connector. Hence the disclosed cap can be mounted onto both male and female luers. The threads of the inner cap and the threads of the outer cap have little or no interference with each other, and the dimension of the threads of the inner cap and the threads of the outer cap are independent with each other while meeting the luer standard.

The device can achieve disinfection when used on luer connectors by integrating disinfectant or antimicrobial agent in the chamber of the outer cap. The disinfectant or antimicrobial agent can be directly included in the chamber or disinfectant or antimicrobial agent can be absorbed into sponges or foam material that fills the chamber of outer cap. In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In one or more embodiments, the disinfectant or antimicrobial agent may be a fluid or a gel. In one or more embodiments, the absorbent material compresses toward the closed end of the chamber upon connection to the female luer connector or the male luer connector. The compression of the absorbent material disinfects the female luer connector or the male luer connector.

The peelable seal on the end face to prevent the disinfectant or the antimicrobial agent from exiting the chamber.

In one or more embodiments, the outer cap exterior wall surface includes a plurality of grip members.

Another aspect of the present disclosure pertains to a device for connection to a medical connector according to a fourth exemplary embodiment of the present disclosure generally comprises an outer cap, an inner cap, and a peelable seal.

The outer cap comprises an integral body, a closed end, an annular wall having a length extending from the closed end to an open end and defining a chamber containing an absorbent material and disinfectant or antimicrobial agent. The open end of the outer cap defines an end face.

The annular wall of the outer cap comprises an outer cap exterior wall surface and an outer cap interior wall surface. The outer cap interior wall surface includes one or more pockets.

The inner cap comprises an integral body having an annular wall having an exterior wall surface and an interior wall surface with a first end of the inner cap facing the closed end of the outer cap, a second end of the inner cap facing the open end of the outer cap. The exterior wall surface of the first end of the inner cap includes a flexure hinge adapted to engage the one or more pockets of the interior wall surface of the outer cap to fix the position of the inner cap with the outer cap. The exterior wall surface of the second end of the inner cap includes one or more threads adapted to engage a male luer connector.

The peelable seal on the end face to prevent the disinfectant or the antimicrobial agent from exiting the chamber.

In one or more embodiments, the open end of the outer cap is situated on a same horizontal plane as the second end of the inner cap in an initial state.

In one or more embodiments, when a male luer connector is engaged to the one or more threads of the exterior wall surface of the second end of the inner cap and rotated in a clockwise direction, the flexure hinge on the inner cap disengages from the pocket on the outer cap interior wall surface to allow the inner cap to partially protrude out from the opening end of the outer cap.

In one or more embodiments, when a male luer connector is engaged to the one or more threads of the exterior wall surface of the second end of the inner cap and rotated in a counter-clockwise direction, the inner cap retracts into the chamber of the outer cap.

In one or more embodiments, when a female luer connector is engaged to the device, the inner cap will be pushed and the interlocking between the flexure hinge on the inner cap and the pocket on the outer cap will be dislodged to allow the inner cap to move toward the closed end of the chamber.

In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

In one or more embodiments, the outer cap exterior wall surface includes a plurality of grip members.

In one or more embodiments, the female luer connector is selected from the group consisting of needle-free connectors, stopcocks, and hemodialysis connectors.

In one or more embodiments, the male luer connector may be an intravenous tubing end, stopcock or male lock luer.

Another aspect of the present disclosure pertains to a device for connection to a medical connector according to a fifth exemplary embodiment of the present disclosure generally comprises an outer cap, an inner cap, and a peelable seal.

The outer cap comprises an integral body, a closed end, an annular wall having a length extending from the closed end to an open end and defining a chamber containing an absorbent material and disinfectant or antimicrobial agent. The open end of the annular wall defines an end face. In one or more embodiments, the annular wall comprises a flared curvature at the open end of the body defining an end face. The annular wall of the outer cap comprises an outer cap exterior wall surface and an outer cap interior wall surface, the interior wall surface having one or more protrusions. The inner cap comprises an integral body having an annular wall having an exterior wall surface and an interior wall surface with a first end of the inner cap facing the closed end of the outer cap, a second end of the inner cap facing the open end of the outer cap. The exterior wall surface of the first end of the inner cap includes a dimple adapted to engage the one or more protrusions of the interior wall surface of the outer cap to fix the position of the inner cap with the outer cap. The exterior wall surface of the second end of the inner cap includes one or more thread-tabs adapted to engage a male luer connector. The peelable seal on the end face to prevent the disinfectant or the antimicrobial agent from exiting the chamber.

In one or more embodiments, the outer cap exterior wall surface can include indicia, graphics, symbols, diagrams, words or other instructions.

In one or more embodiments, the open end of the outer cap may be situated on a same horizontal plane as the second end of the inner cap in an initial state.

When a male luer connector is engaged to the one or more threads of the exterior wall surface of the second end of the inner cap and rotated in a clockwise direction, the inner cap partially protrude out from the open end of the outer cap.

When a male luer connector is engaged to the one or more threads of the exterior wall surface of the second end of the inner cap and rotated in a counter-clockwise direction, the inner cap retracts into the chamber of the outer cap.

When a female luer connector is engaged to the device, the inner cap slips and retracts into the chamber of the outer cap.

In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

In one or more embodiments, the outer cap exterior wall surface includes a plurality of grip members.

In one or more embodiments, the female connector is selected from the group consisting of needle-free connectors, stopcocks, and hemodialysis connectors.

In one or more embodiments, the male connector may be an intravenous tubing end, stopcock or a male lock luer.

BRIEF DESCRIPTION OF THE DRAWINGS

FIG. 33 shows a perspective view of a device according to a fifth embodiment in connection with a male luer connector; and FIG. 34 shows a perspective view of a device according to a fifth embodiment in connection with a female luer connector.

DETAILED DESCRIPTION

Before describing several exemplary embodiments of the disclosure, it is to be understood that the disclosure is not limited to the details of construction or process steps set forth in the following description. The disclosure is capable of other embodiments and of being practiced or being carried out in various ways.

Embodiments of the disclosure pertain to a universal single-use device for connection to and disinfection of a medical connector, including male luer connectors and female luer connectors, in which the device comprises an outer cap and inner luer. The device provides a mechanical barrier for connectors and contains an antimicrobial agent for disinfection. The device of the present disclosure allows the practitioner to streamline the disinfecting process.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

Figure 1:
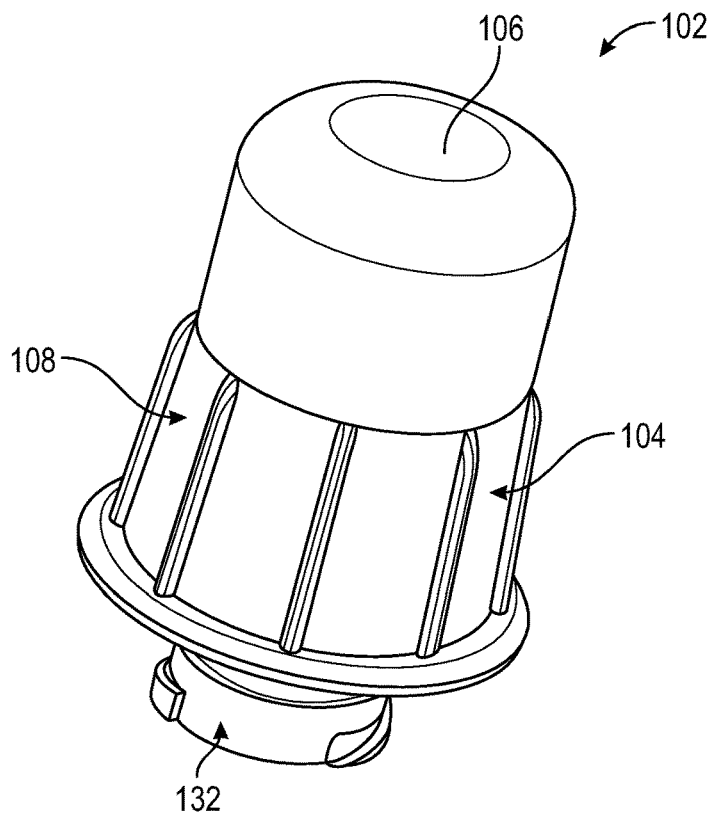
FIG. 1 shows a top perspective view of a device according to a first embodiment.
Figure 2:
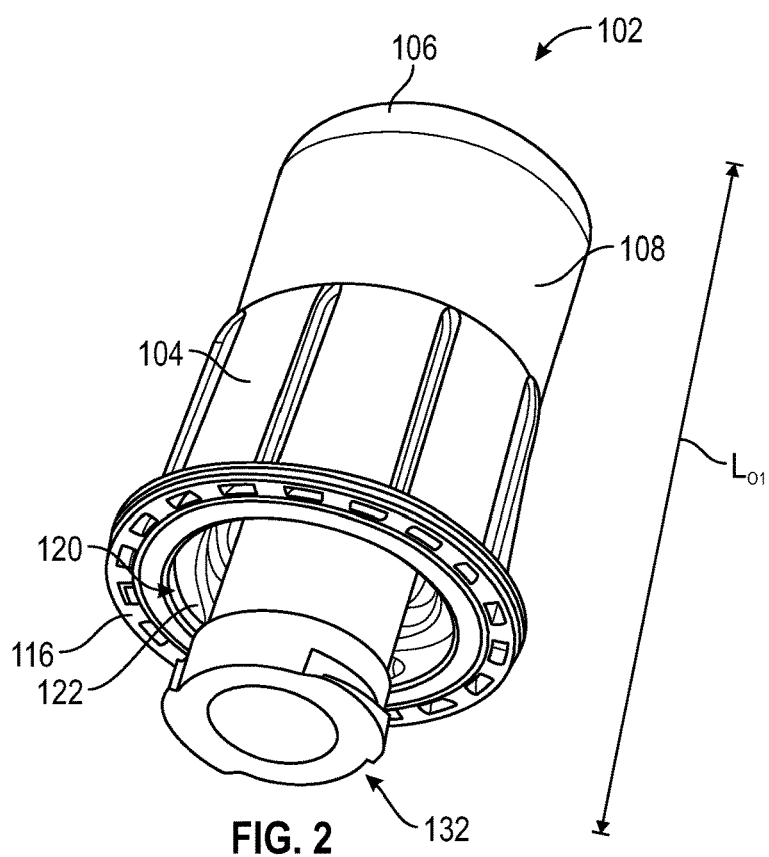
FIG. 2 illustrates a bottom perspective view of the device shown in FIG. 1.
Figure 4:
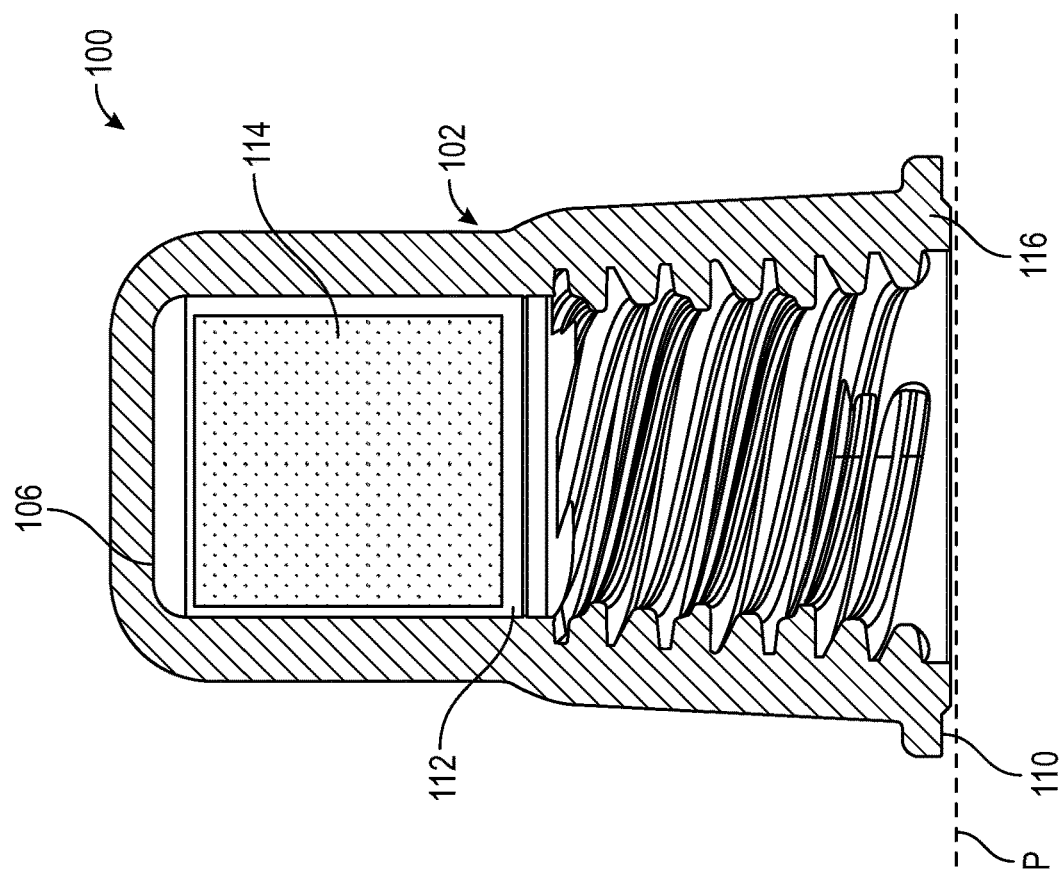
FIG. 4 illustrates a side view of an outer cap.
Figure 3:
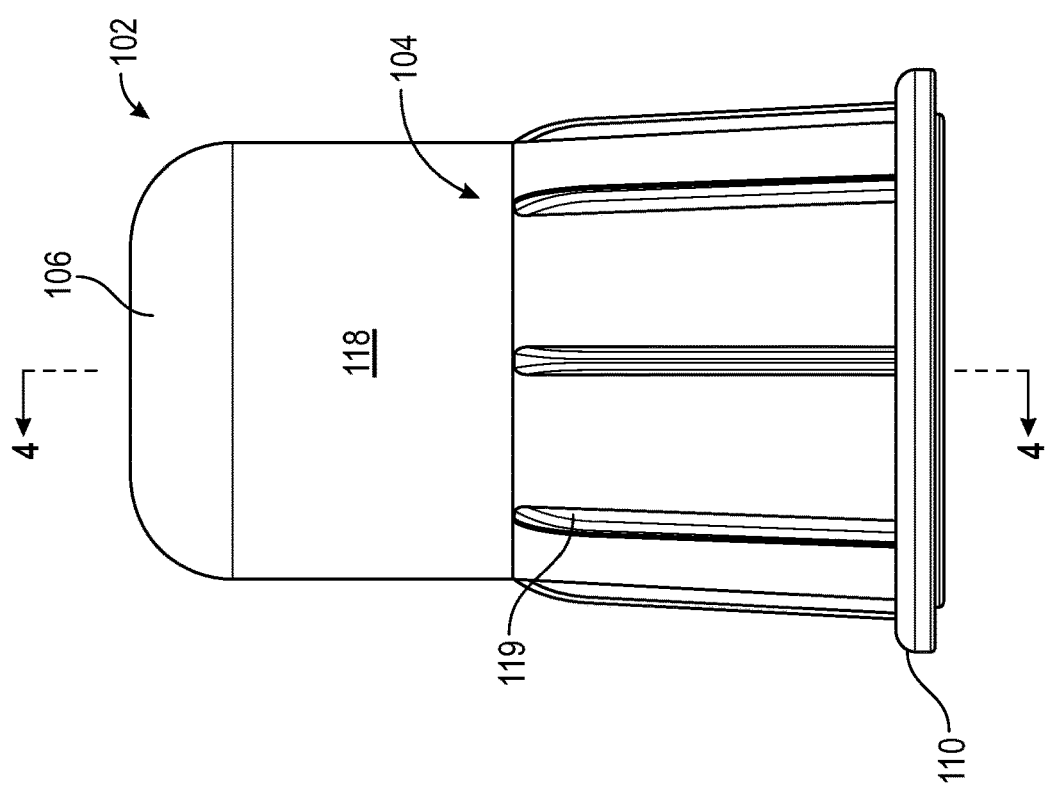
FIG. 3 illustrates a side view of a device according to a first embodiment.
Figures 5, 6, 7:
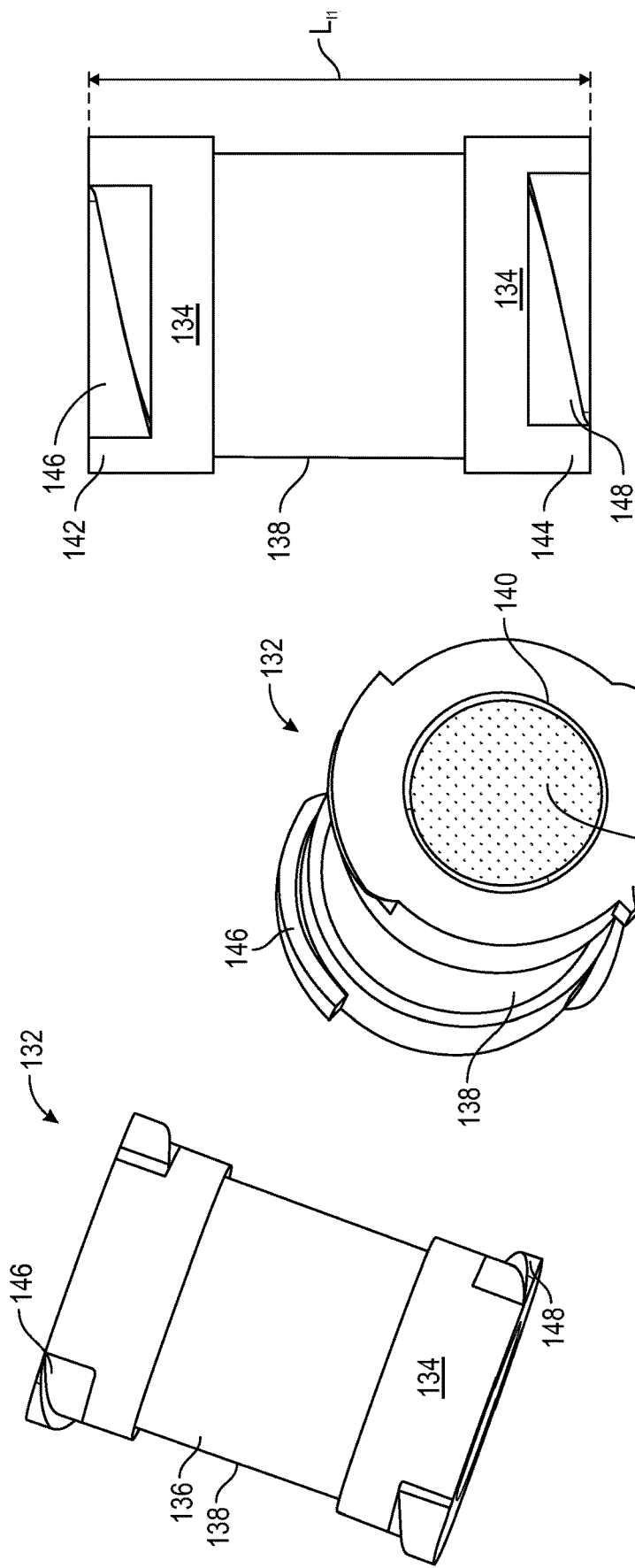
FIG. 5 illustrates a perspective side view of an inner cap of the device shown in FIG. 1.
FIG. 6 illustrates a perspective bottom view of an inner cap of the device shown in FIG. 1.
FIG. 7 illustrates a side view of an inner cap of the device shown in FIG. 1.
Figure 8:
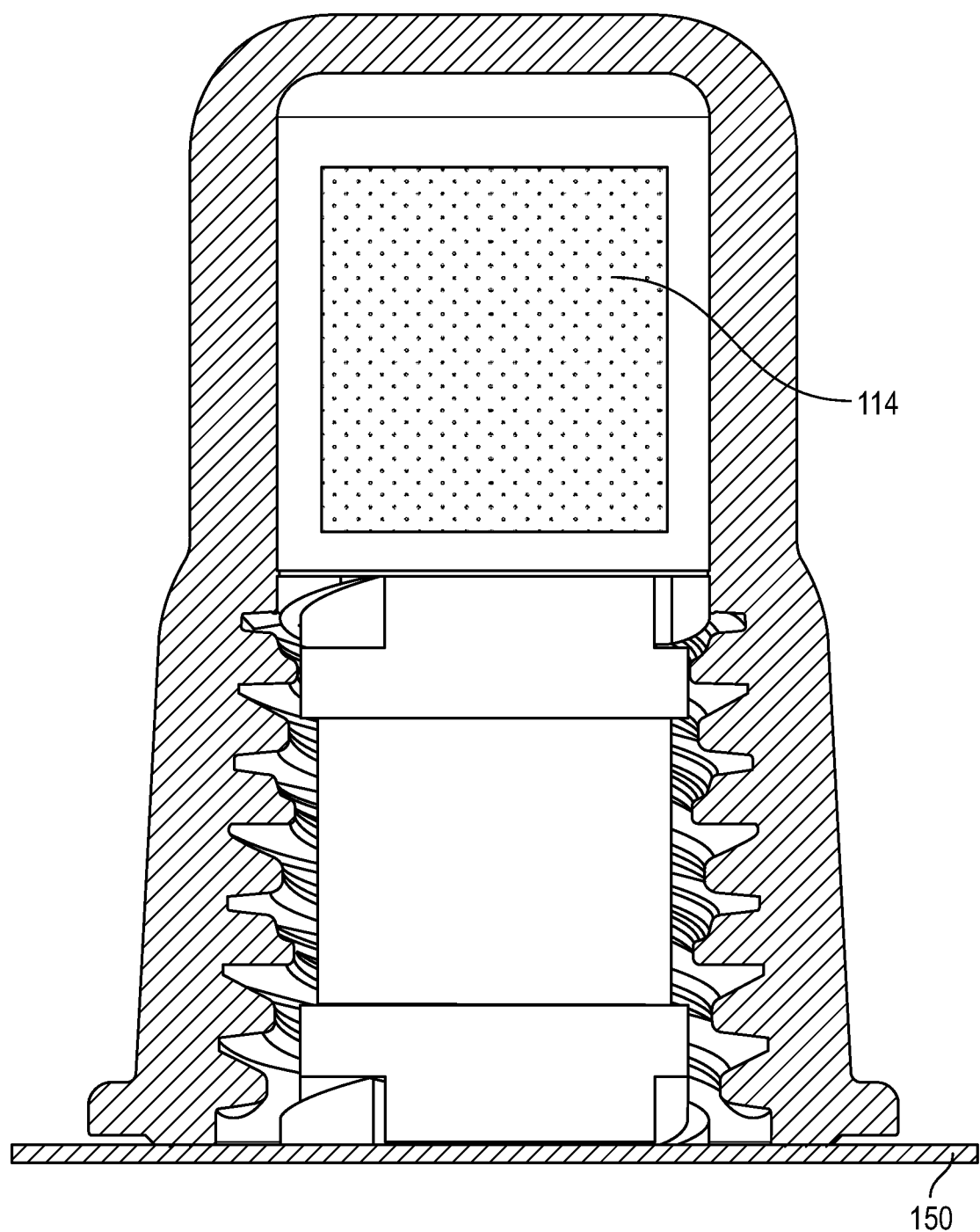
FIG. 8 illustrates a cross-sectional view of the device shown in FIG. 1 with an absorbent material.
Figure 10:
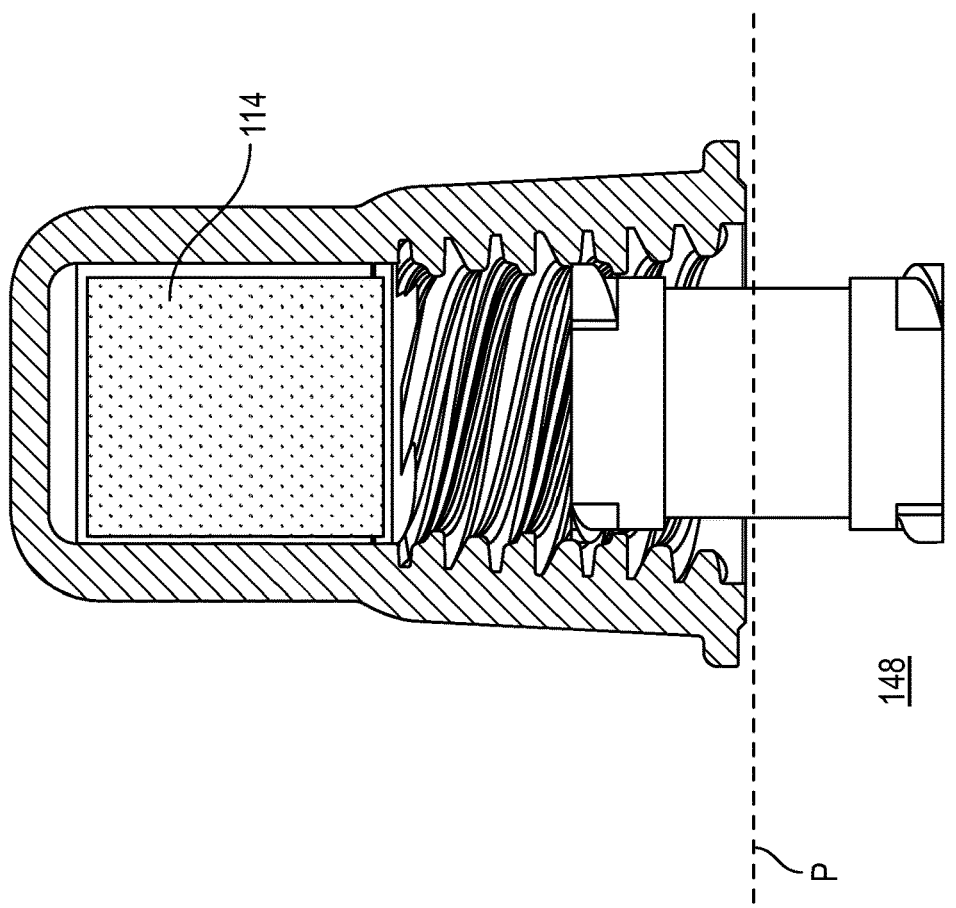
FIG. 10 illustrates a cross-sectional view of the device shown in FIG. 1 with male luer connector activation.
Figure 9:
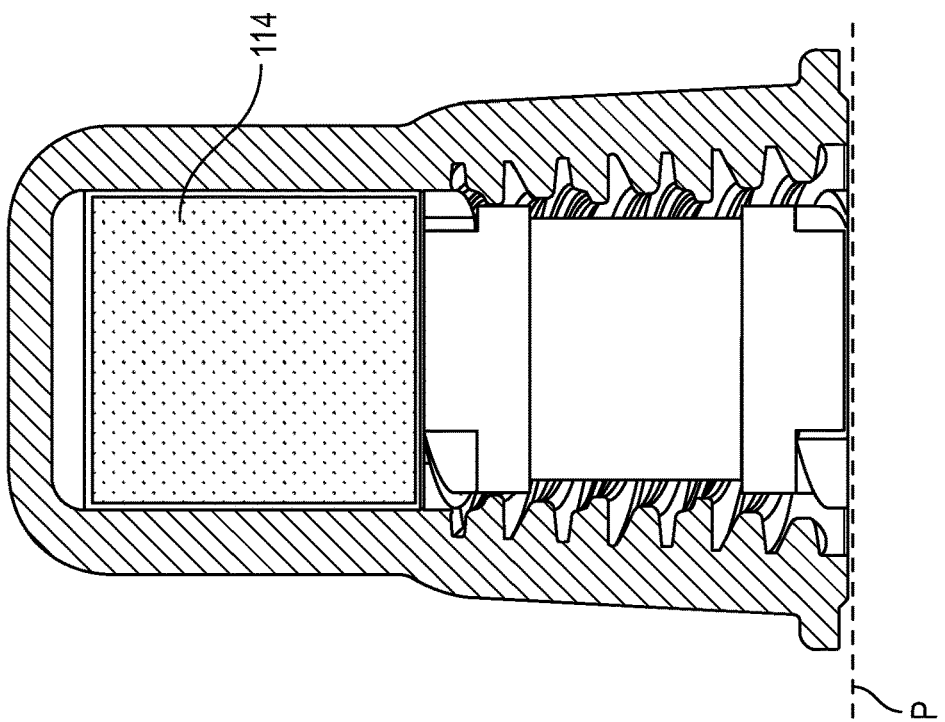
FIG. 9 illustrates a cross-sectional view of the device shown in FIG. 1 in an initial state.

Referring to FIGS. 1-10, a device 100 for connection to a medical connector according to a first exemplary embodiment of the present disclosure generally comprises an outer cap 102, an inner cap 132, and a peelable seal 150. In one or more embodiments, as shown in FIG. 2 and FIG. 4, the outer cap 102 comprises an integral body 104, a closed end 106, and an outer cap annular wall 108 having a length $L_{O1}$ extending from the closed end 106 to an open end 110 defining a chamber 112. The chamber 112 may contain an absorbent material 114 and disinfectant or antimicrobial agent. The open end 110 of the outer cap 102 defines an end face 116. The annular wall 108 of the outer cap 102 includes an outer cap exterior wall surface 118 and an outer cap interior wall surface 120. The outer cap interior wall surface 120 includes one or more threads 122 adapted to engage a female luer connector. The inner cap 132 includes an integral body 134 having an annular wall 136 having an exterior wall surface 138 and an interior wall surface 140 with a first end 142 of the inner cap facing the closed end 106 of the outer cap 102, a second end 144 of the inner cap facing the open end 110 of the outer cap 102. The inner cap annular wall 136 having a length $L_{I1}$ extending from the first end 142 to the second end 144 and being less than the length $L_{O1}$ of the outer cap. The exterior wall surface 138 of the first end 142 of the inner cap 132 includes one or more threads 146 to engage with the threads 122 on the interior wall surface 120 of the outer cap 102. The exterior wall surface 138 of the second end 144 of the inner cap 132 includes one or more threads 148 adapted to engage a male luer connector. When the threads of the inner cap are engaged with a male luer connector, the threads of the outer cap will be passive. Alternatively, when the threads of the outer cap are engaged with a female luer connector, the threads of the inner cap will be passive. In one or more embodiments, the peelable seal 150 may be placed on the end face to prevent the disinfectant or the antimicrobial agent from exiting the chamber 112. In one or more embodiments, the peelable seal comprises an aluminum or multi-layer polymer film peel back top. In one or more embodiments, the peelable seal 150 comprises a moisture barrier.

When device 100 is removed from its packaging, the open end 110 of the outer cap 102 is situated on approximately a same horizontal plane P as the second end 144 of the inner cap 132 in an initial state. As used herein, the use of the phrase "approximately a same horizontal plane P" refers to a position in which the outer cap and the inner cap are close to each other but the inner cap does not protrude relative to the outer cap. To connect the device to a male luer connector, the user applies an axial load such that a male luer connector is engaged to the one or more threads 148 of the exterior wall surface 138 of the second end 144 of the inner cap 132 and rotated in a clockwise direction, the inner cap 132 partially protrudes out from the open end of the outer cap. When the inner cap 132 partially protrudes out from the open end 110 of the outer cap 102, there is no space that exists between the device and the connector. When a male luer connector is engaged to the one or more threads 148 of the exterior wall surface 138 of the second end 144 of the inner cap 132 and rotated in a counter-clockwise direction, the inner cap 132 retracts into the chamber 112 of the outer cap 102. In one or more embodiments, male luer connector can be detached from device 100 by counter-clockwise rotation without forcing inner cap 132 to retract. When a female luer connector is engaged to the device, the inner cap 132 slips and retracts into the chamber 112 of the outer cap 102. Once the device is engage to the connector, the device may be removed from the connector by rotating the device counter-clockwise. Upon disengagement, the inner cap 132 and the outer cap 102 remain intact and attached to each other.

Device 100 is designed to be compatible in interacting with various disinfectants. In one or more embodiments, the disinfectant or antimicrobial agent may include variations of alcohol or chlorhexidine. The disinfectant or antimicrobial agent can be a fluid or a gel selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

In one or more embodiments, the absorbent material compresses toward the closed end of the chamber upon connection to the female luer connector or the male luer connector. The compression of the absorbent material disinfects the female luer connector or the male luer connector.

The inner cap 132 and/or the outer cap 102 is made from any of a number of types of plastic materials such as polycarbonate, polypropylene, polyethylene, glycol-modified polyethylene terephthalate, acrylonitrile butadiene styrene or any other moldable plastic material used in medical devices.

In one or more embodiments, the outer cap exterior wall surface 118 includes a plurality of grip members 119.

In one or more embodiments, the female connector may be a needle-free connector, stopcock, or hemodialysis connector. In one or more embodiments, the needleless connector is selected from a Q-SYTLE connector, MAXPLUS, MAXPLUS CLEAR, MAXZERO, ULTRASITE, CARESITE, INVISION-PLUS, SAFELINE, ONELINK, V-LINK, CLEARLINK, NEUTRACLEAR, CLAVE, MICROCLAVE, MICROCLAVE CLEAR, NEUTRON, NANOCLAVE, KENDALL, NEXUS, INVISION, VADSITE, BIONECTOR, etc. In one or more embodiments, the male connector may be an intravenous tubing end or stopcock.

Referring to FIGS. 11-20, a device 200 for connection to a medical connector according to a second exemplary embodiment of the present disclosure generally comprises an outer cap 202, an inner cap 232, and a peelable seal. As discussed further herein, device 200 can fit a broad range of luer fitting, including closed female luer, open female luer, and male luer fittings, while is capable of disinfecting the medical implement such as access ports including needleless connectors, male connectors on intravenous lines, stopcocks, and hemodialysis connectors. The inner cap 232 is in a slidable arrangement with the outer cap 202.

Figure 12:
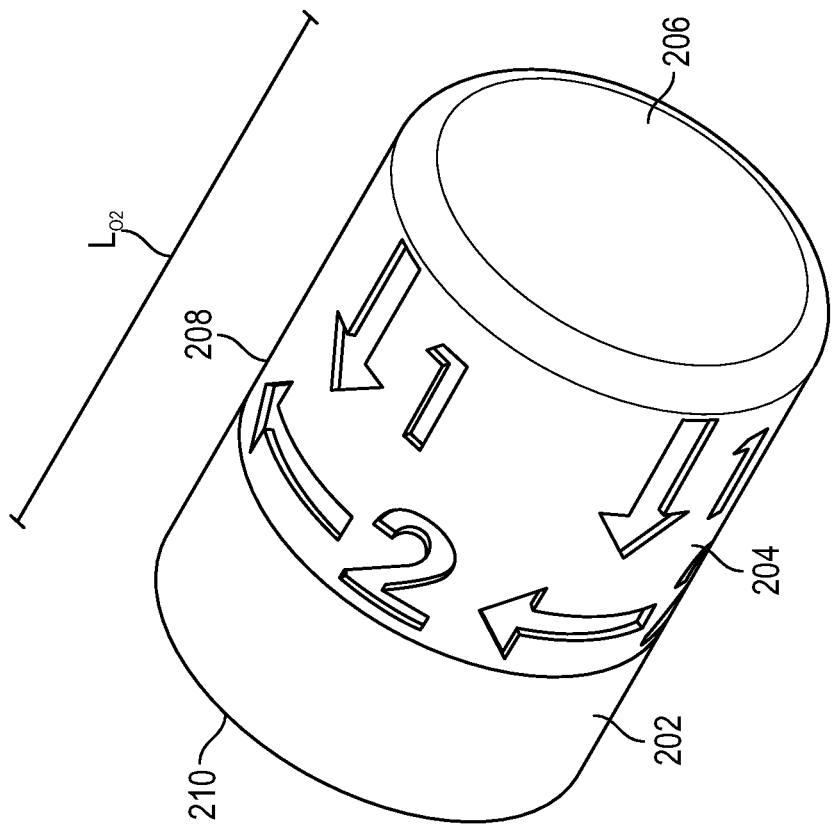
FIG. 12 illustrates a top perspective view of the device shown in FIG. 11.
Figure 11:
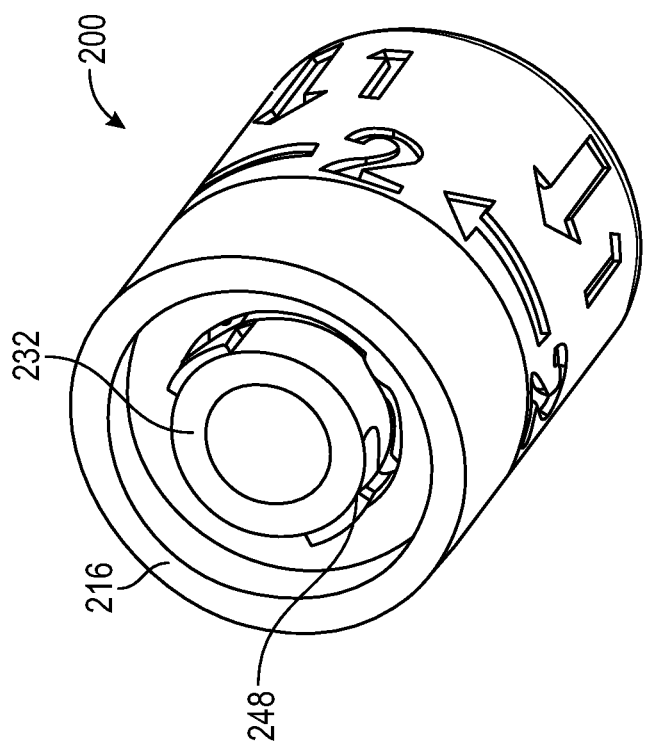
FIG. 11 shows a bottom perspective view of a device according to a second embodiment.
Figure 13:
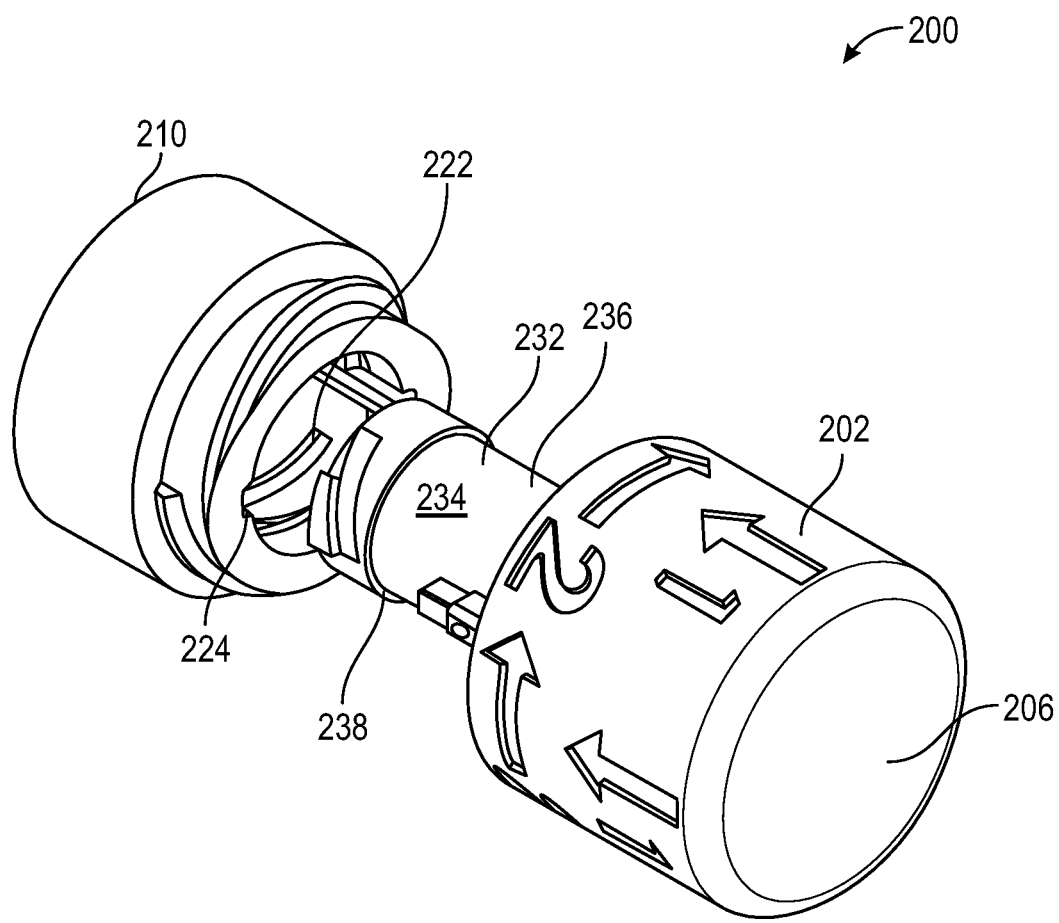
FIG. 13 shows an exploded side perspective view of a device according to a second embodiment.
Figure 15:
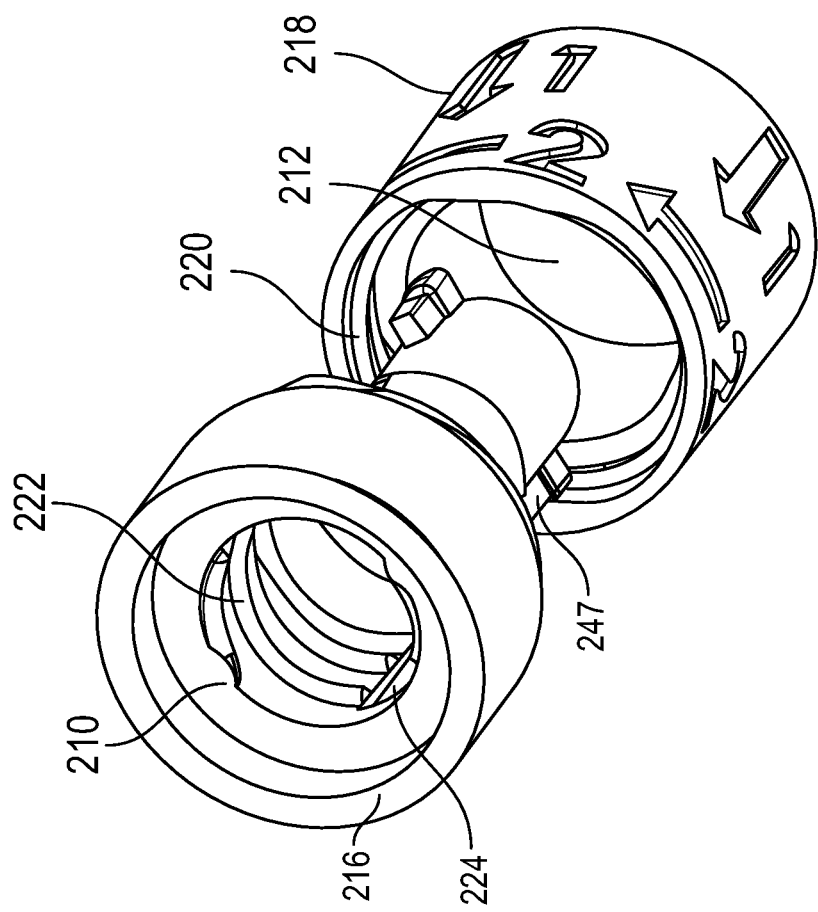
FIG. 15 shows an exploded bottom perspective view of a device according to a second embodiment.
Figure 14:
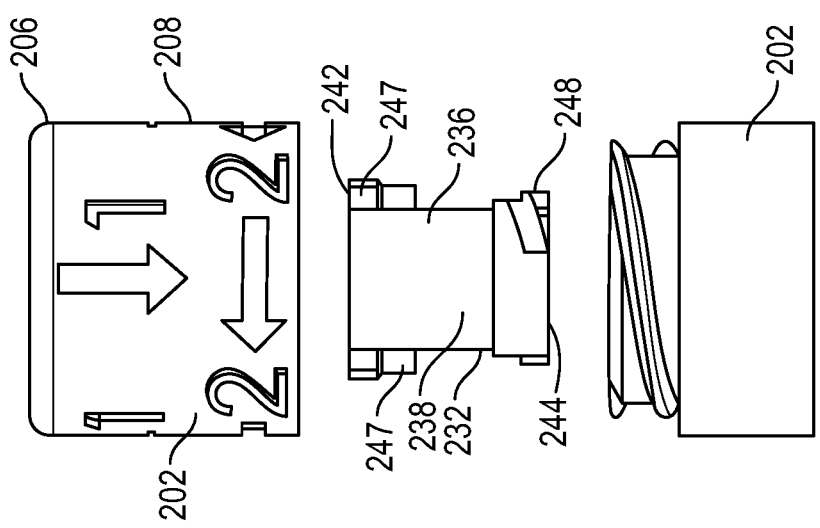
FIG. 14 shows an exploded side view of a device according to a second embodiment.
Figure 17:
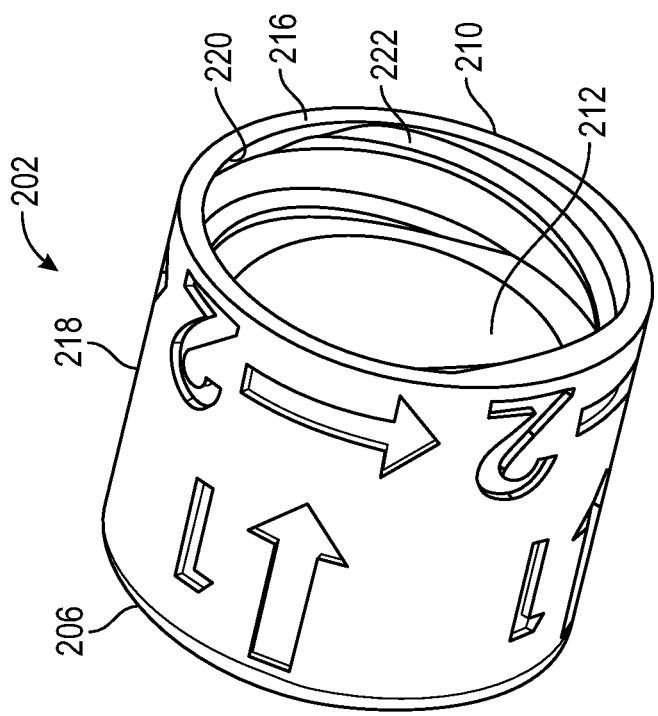
FIG. 17 shows an perspective bottom view of an outer cap of a device according to a second embodiment.
Figure 16:
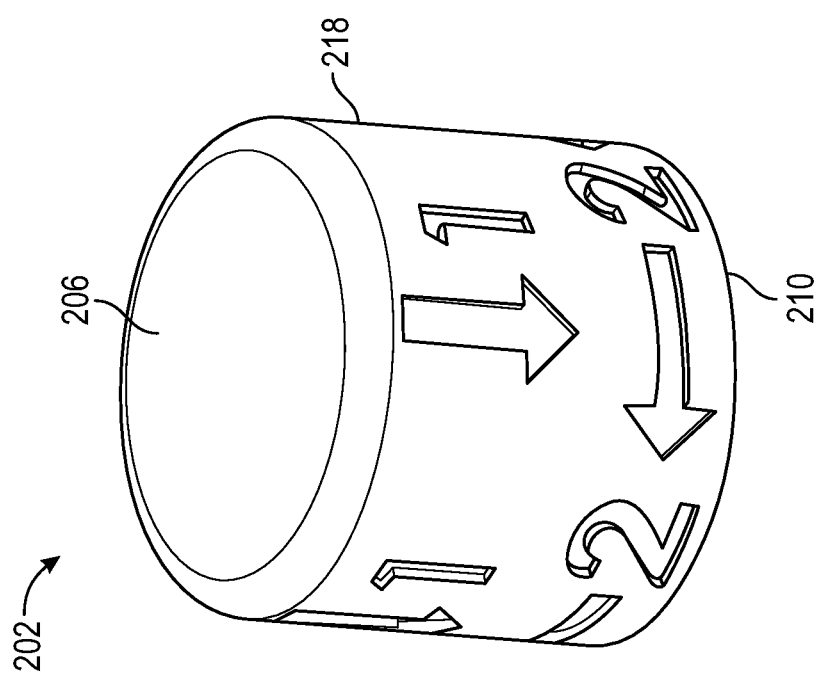
FIG. 16 shows an perspective top view of an outer cap of the device according to a second embodiment.
Figure 18:
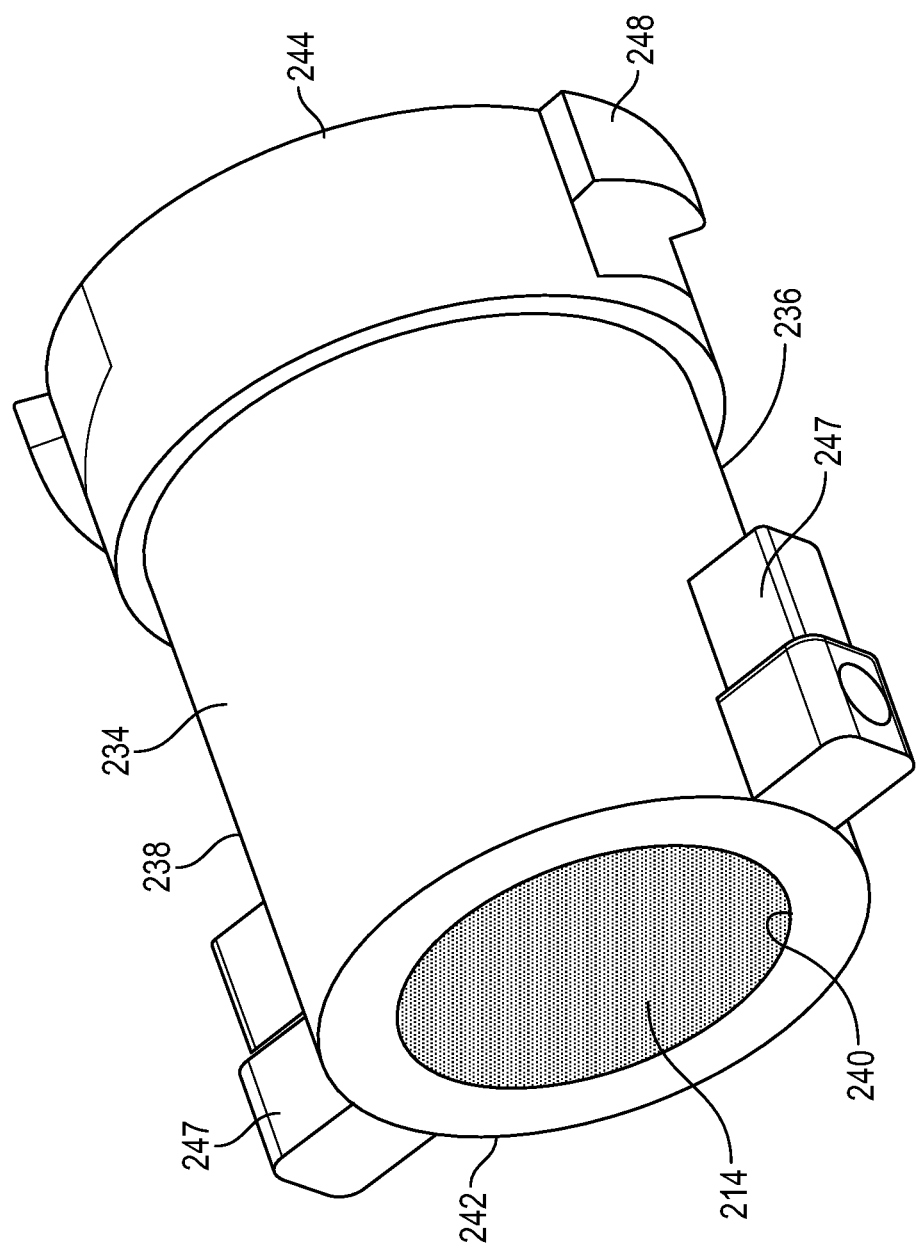
FIG. 18 shows an perspective view of an inner cap of a device according to a second embodiment.
Figure 19:
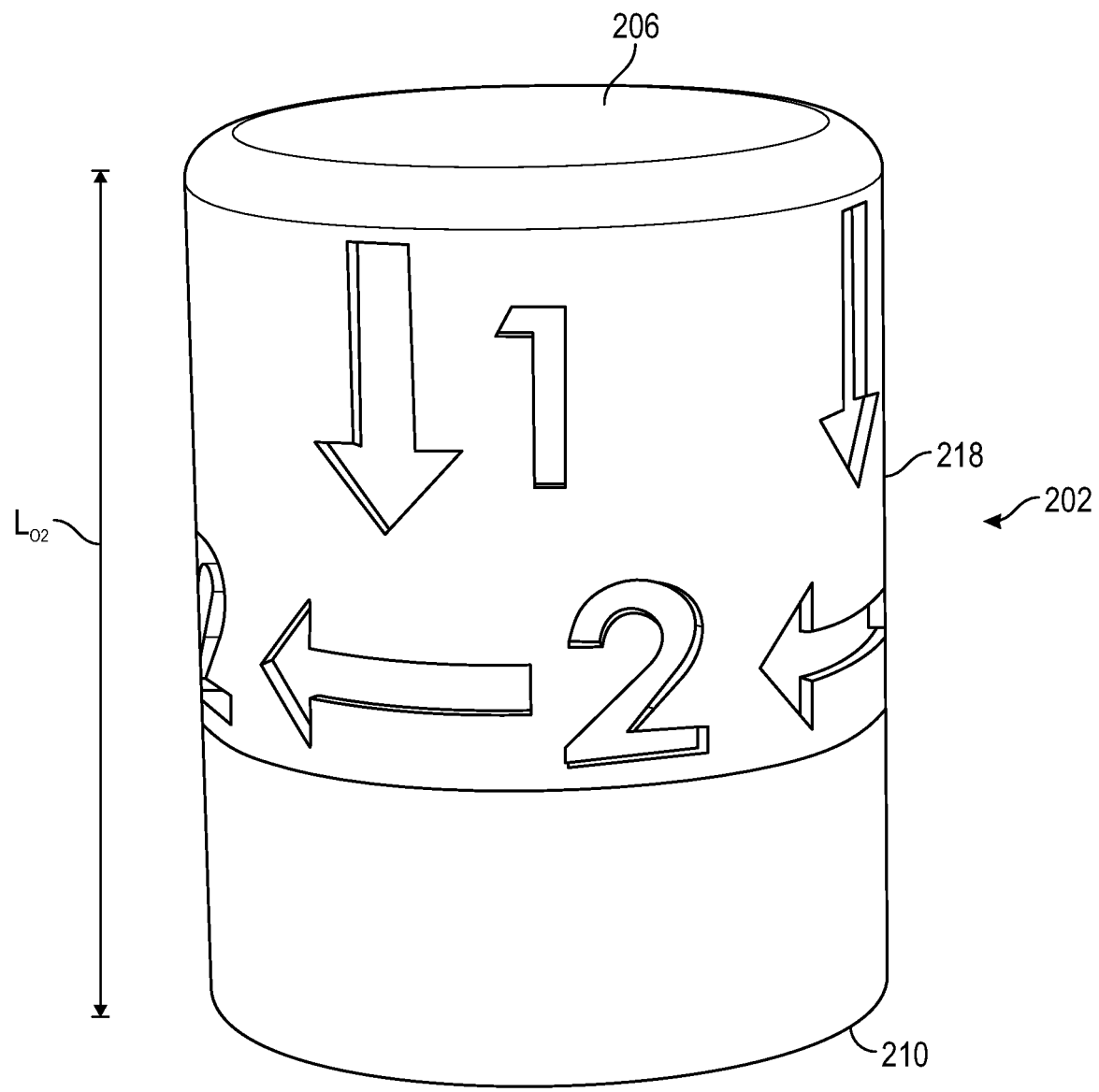
FIG. 19 shows an perspective view of a device according to a second embodiment.
Figure 20:
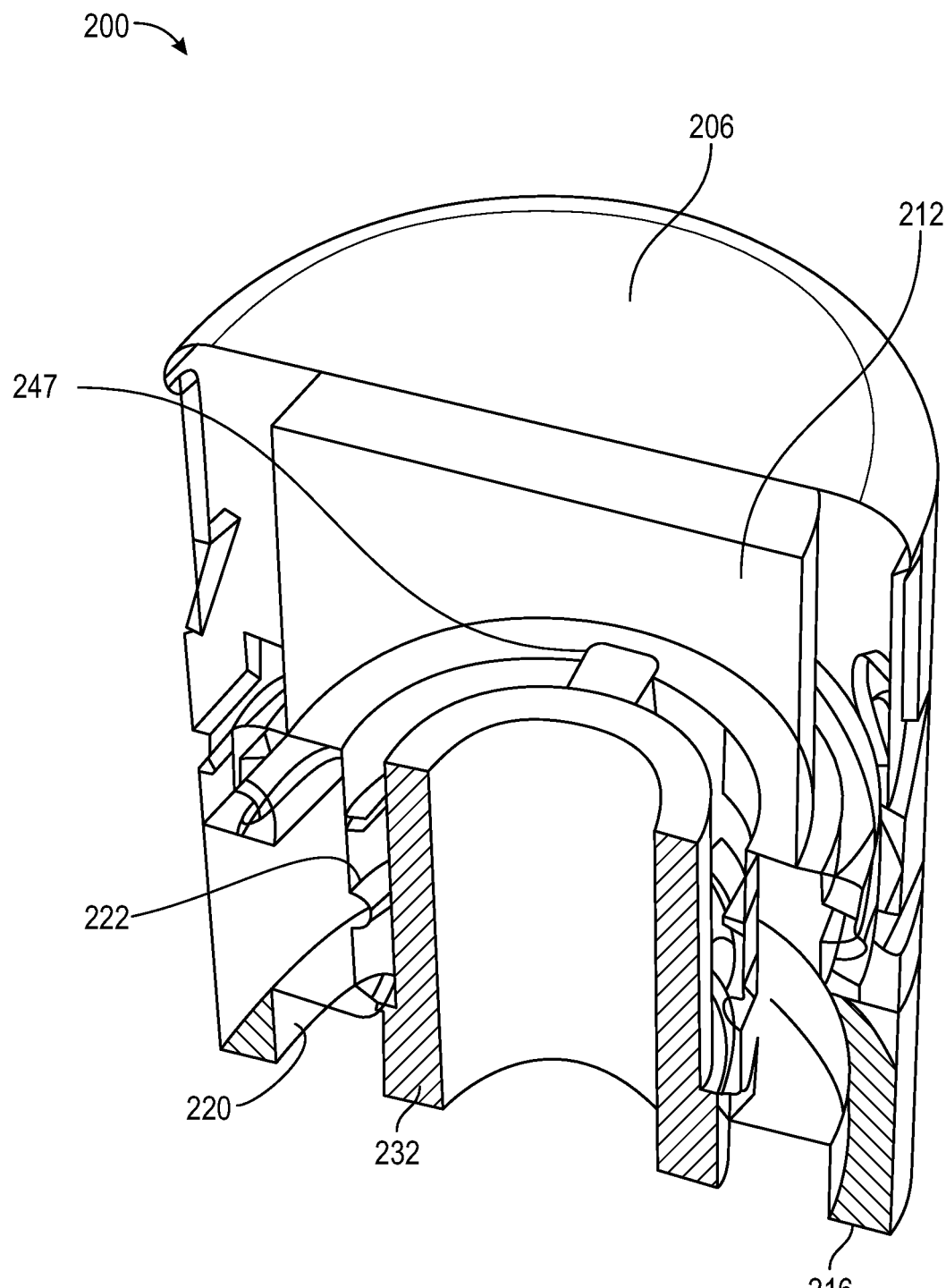
FIG. 20 shows a cross-sectional view of an inner cap of a device according to a second embodiment.
Figure 21:
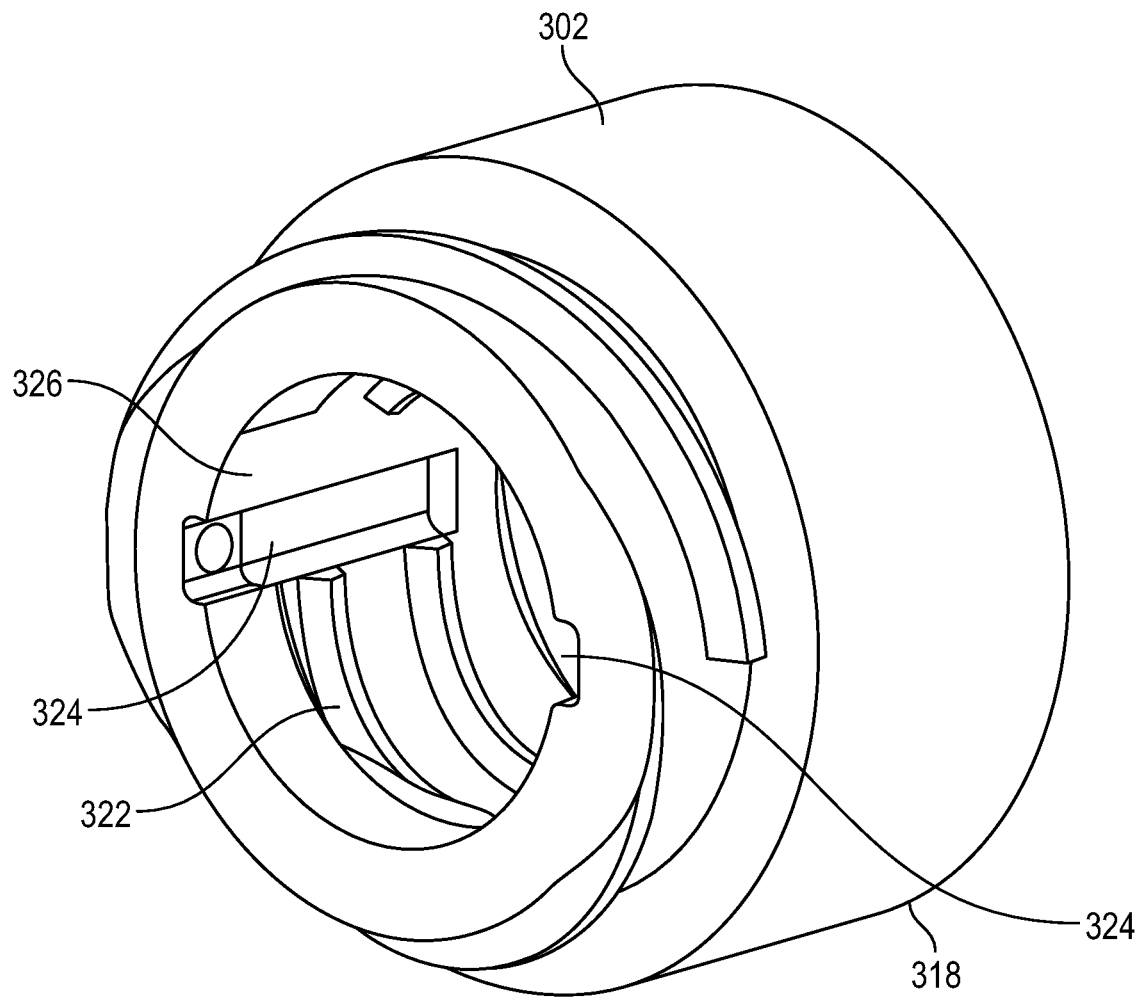
FIG. 21 shows a perspective view of an outer cap according to a third embodiment.
Figure 22:
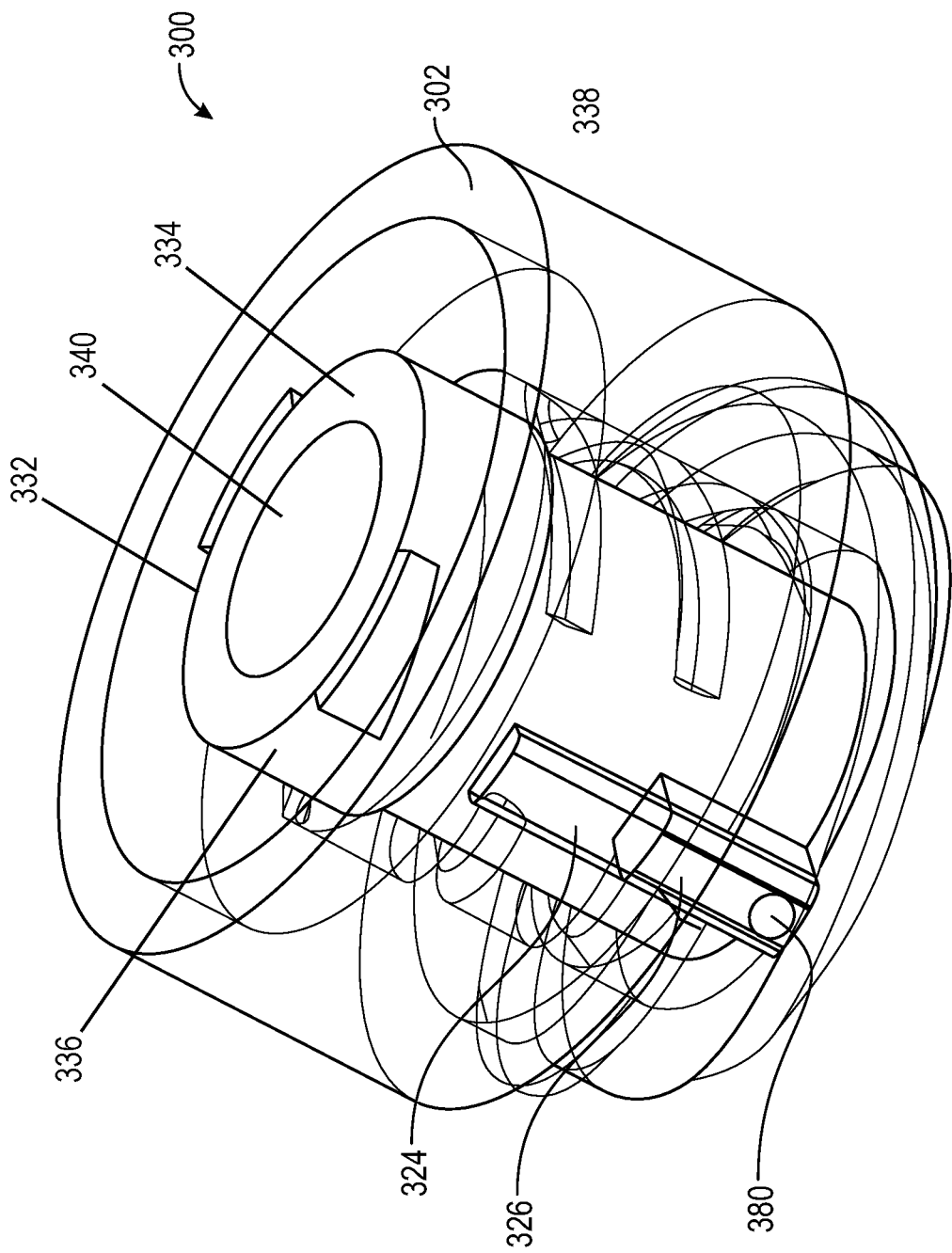
FIG. 22 shows a sectional view of a device according to a third embodiment.
Figure 23:
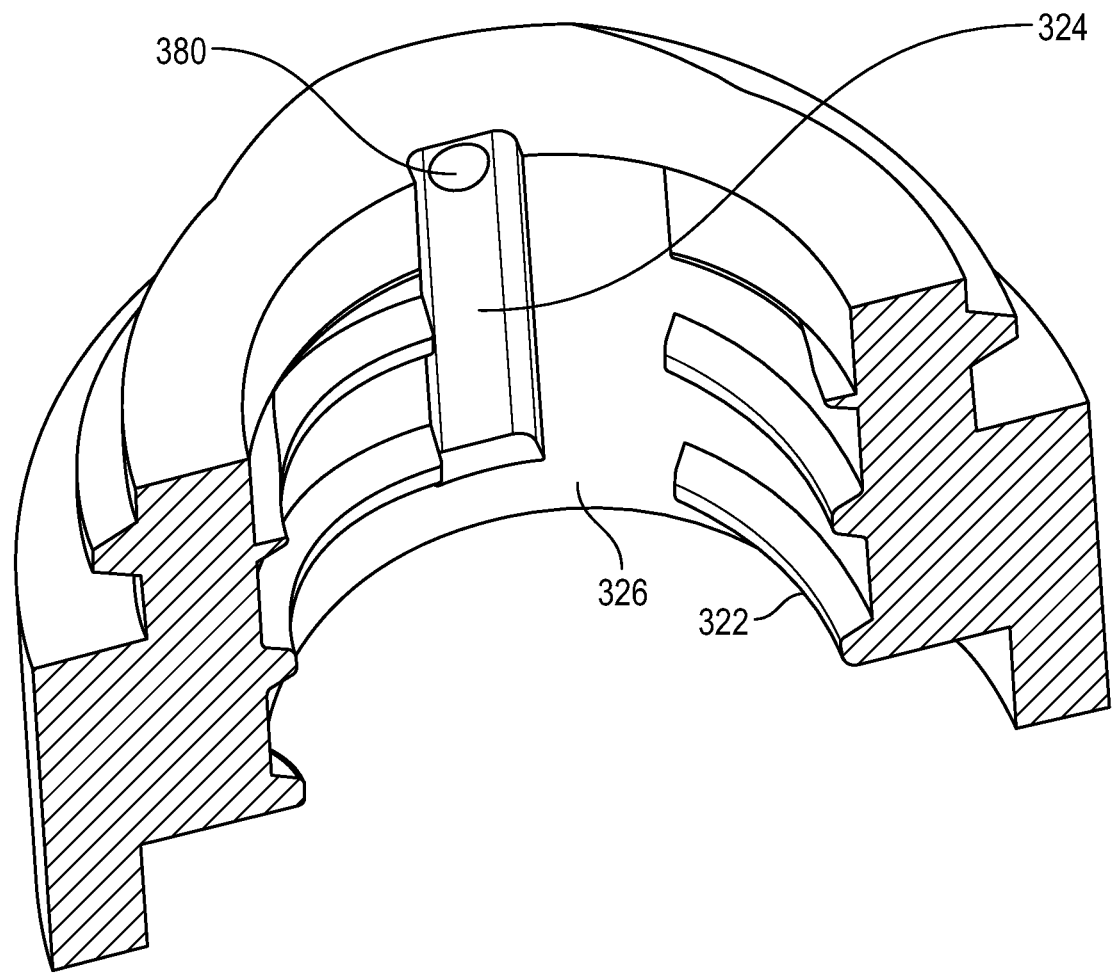
FIG. 23 shows a cross-sectional view of an outer cap of a device according to a third embodiment.
Figure 24:
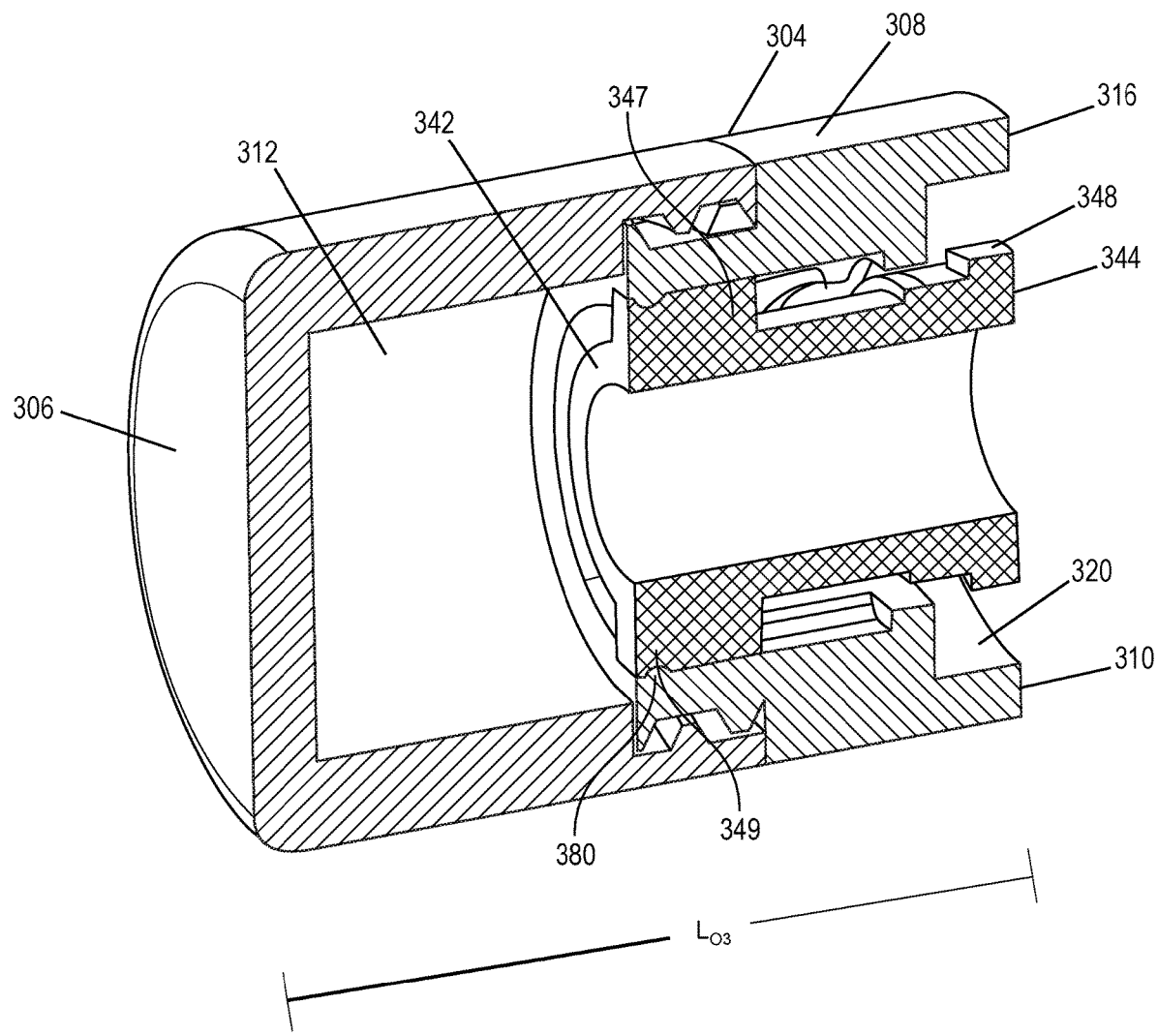
FIG. 24 shows a cross-sectional view of a device according to a third embodiment.

As shown in FIGS. 12-15, the outer cap 202 comprises a body 204, a closed end 206, an outer cap annular wall 208 having a length $L_{O2}$ extending from the closed end 206 to an open end 210 and defining a chamber 212 containing an absorbent material and disinfectant or antimicrobial agent. The open end 210 defines an end face 216. Outer cap annular wall 208 includes an outer cap exterior wall surface 218 and an outer cap interior wall surface 220. The outer cap interior wall surface 220 comprises one or more grooves 224 and one or more threads 222 adapted to engage with a female luer connector. In one or more embodiments, the female connectors may be in the form of needle-free connectors, stopcocks, and hemodialysis connectors. In one or more alternate embodiments, as shown in FIG. 12, the body 204 of the outer cap 202 may be comprised of two components, where a rear-end component with an inner cavity is screwed onto the front-end component of the cap body via threads or welding.

The inner cap 232 comprises a body 234 having an annular wall 236 having an exterior wall surface 238 and an interior wall surface 240 with a first end 242 of the inner cap facing the closed end 206 of the outer cap 202. A second end 244 of the inner cap 232 faces the open end 210 of the outer cap 202. The outer cap interior wall surface 220 comprises one or more grooves 224 along which the inner cap 232 is able to slide. The exterior wall surface 238 of the first end 242 of the inner cap 232 includes two shaft-like wings 247 to fit into the one or more grooves 224 of the outer cap interior wall surface 220 and facilitate the slide motion without allowing signification relative rotation between the inner cap 232 with respect to the outer cap 202. The outer-most diameter of the threads of the inner cap is designed to have minimum interference, e.g. sliding fit or strip fit, with the threads of the outer cap to allow relative linear motion and also facilitate assembly of device 200. The teeth depth of the threads of the inner cap and the outer cap is desired to be sufficient to engage with the male and female luer connectors. The exterior wall surface 238 of the second end 244 of the inner cap 232 includes one or more thread-tabs 248 adapted to engage a male luer connector. In one or more embodiments, the exterior wall surface 238 of the second end 244 of the inner cap 232 includes two thread-tabs 248 adapted to engage a male luer connector. The male luer connectors include collars with female threads. In one or more embodiments, the male connector can be an intravenous (I.V.) tubing end, stopcock or male lock luer.

Inner cap 232 can slide back and forth with respect to outer cap 202. In one or more embodiments, the open end 210 of the outer cap 202 is situated on a same horizontal plane P as the second end 244 of the inner cap 232 in an initial state. When a male luer connector is engaged to the one or more thread-tabs 248 of the exterior wall surface 238 of the second end 244 of the inner cap 232, the inner cap 232 slides against the outer cap 202 to partially protrude out from the open end 210 of the outer cap 202. When a female luer connector is engaged to device 200, the inner cap 232 slides against the outer cap 202 and retracts into the chamber 212 of the outer cap 202 to allow the female luer connector to engage the one or more threads 222 on the interior wall surface 220 of the outer cap 202.

The inner cap 232 and/or the outer cap 202 is made from any of a number of types of plastic materials such as polycarbonate, polypropylene, polyethylene, glycol-modified polyethylene terephthalate, acrylonitrile butadiene styrene or any other moldable plastic material used in medical devices.

Disinfecting caps currently on the market are capable of only disinfecting one of the three types of luer fitting, namely female luer of needle-free connectors, female luer of stopcocks, and male luer connectors on intravenous injection sites. Thus, to avoid having to use different types of disinfecting caps to clean different types of connectors, device 200 is self-adaptive to different types of luer connectors due to the sliding mechanism between the inner cap that engages with male luer connectors and the outer cap that engages with female luer connectors thereby allowing the user to clean different types of connectors with a single device. As discussed above, upon mounting the outer cap 202 onto female luer connectors, the inner cap 232 retreats towards the chamber 212 at the closed end 206 of the outer cap 202, thus, providing space for female luer connectors to be inserted and screwed onto the threads 222 of the outer cap 202. Upon mounting the inner cap 232 of device 200 onto a male luer connector, the one or more thread-tabs 248 on the exterior wall surface 238 of the second end 244 of the inner cap 232 engage with the threads on the male luer connector. Hence the disclosed cap can be mounted onto both male and female luers.

The device 200 can achieve disinfection when used on luer connectors by integrating disinfectant or antimicrobial agent in the chamber of the outer cap. The disinfectant or antimicrobial agent can be directly included in the chamber or disinfectant or antimicrobial agent can be absorbed into sponges or foam material that fills the chamber of outer cap. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

The peelable seal on the end face 216 to prevent the disinfectant or the antimicrobial agent from exiting the chamber 212.

In one or more embodiments, the outer cap exterior wall surface 218 includes a plurality of grip members.

The outer-most diameter of the one or more thread-tabs of the inner cap has a minimum interference with the threads of the outer cap to allow for relative linear motion.

Referring to FIGS. 21-24, a device 300 for connection to a medical connector according to a third exemplary embodiment of the present disclosure generally comprises an outer cap 302, an inner cap 332, and a peelable seal. As discussed further herein, device 300 can fit a broad range of luer fitting, including closed female luer, open female luer, and male luer fittings, while is capable of disinfecting the medical implement such as access ports including needleless connectors, male connectors on intravenous lines, stopcocks, and hemodialysis connectors. The inner cap 332 is in a slidable arrangement with the outer cap 302.

The outer cap 302 comprises an integral body 304, a closed end 306, an annular wall 308 having a length $L_{O3}$ extending from the closed end 306 to an open end 310 and defining a chamber 312 containing an absorbent material and disinfectant or antimicrobial agent. The open end defines an end face 316.

The annular wall of the outer cap comprises an outer cap exterior wall surface 318 and an outer cap interior wall surface 320. The outer cap interior wall surface includes one or more grooves 324 and one or more threads 322 adapted to engage with a female luer connector, wherein at least a portion of said one or more threads 322 on the outer cap interior wall surface 320 comprise one or more gaps 326 that does not engage a mating feature of the inner cap 332.

The inner cap 332 slidably engages with the outer cap 302. The inner cap 332 comprises an integral body 334 having an annular wall 336 having an exterior wall surface 338 and an interior wall surface 340 with a first end 342 of the inner cap 332 facing the closed end 306 of the outer cap 302 and a second end 344 of the inner cap 332 facing the open end 310 of the outer cap 302. The exterior wall surface 338 of the first end 342 of the inner cap 332 includes two shaft-like wings 347 to fit into the one or more grooves 324 of the outer cap interior wall surface 320 and facilitate the slide motion without allowing significant relative rotation between the inner cap 332 with respect to the outer cap 302. The exterior wall surface 338 of the second end 344 of the inner cap 332 includes one or more thread-tabs 348 adapted to engage a male luer connector. The inner cap 332 is in a slidable arrangement with the outer cap 302.

The function of the one or more gaps 326 is to accommodate the one or more thread-tabs 348 adapted to engage a male luer connector on the inner cap 332 when sliding motion occurs. The position of the one or more gaps 326, as well as the position of the threads on the inner cap, is to be adjacent to the sliding grooves 324 in order to minimize the gap size and utilize the width of the sliding groove 324 as a part of an accommodation space. The thread-tabs 348 of the inner cap 332 and the threads 322 of the outer cap 302 are no longer restrained by interference therefore enabling a sliding fit. The dimension of threads can be optimized to maximize the engagement between the thread-tabs 348 of the inner cap 332 and the outer cap 302 to the correspondent connectors which improves the mechanical performance of the device when used with connectors in terms of resistance to overriding torque and resistance to axial separation force, hence allowing the device to be more securely attached to luer connectors.

The inner cap 332 and/or the outer cap 302 is made from any of a number of types of plastic materials such as polycarbonate, polypropylene, polyethylene, glycol-modified polyethylene terephthalate, acrylonitrile butadiene styrene or any other moldable plastic material used in medical devices.

The peelable seal on the end face is to prevent the disinfectant or the antimicrobial agent from exiting the chamber.

In one or more embodiments, the open end 310 of the outer cap 302 is situated on a same horizontal plane as the second end 344 of the inner cap 332 in an initial state.

When a male luer connector is engaged to the one or more threads of the exterior wall surface of the second end of the inner cap and rotated in a clockwise direction, the inner cap 332 partially protrude out from the open end 310 of the outer cap 302.

When a male luer connector is engaged to the one or more thread-tabs 348 of the exterior wall surface 338 of the second end 344 of the inner cap 332 and rotated in a counter-clockwise direction, the inner cap 332 retracts into the chamber 312 of the outer cap 302.

When a female luer connector is engaged to the device 300, the inner cap 332 slides against the outer cap 302 and retracts into the chamber 312 of the outer cap 302 to allow the female luer connector to engage the one or more threads 322 on the interior wall surface 320 of the outer cap 302.

In one or more embodiments, the exterior wall surface 338 of the second end 344 of the inner cap 332 includes two thread-tabs 348 adapted to engage a male luer connector having collars with female threads In one or more embodiments, the outer cap exterior wall surface 318 includes a plurality of grip members.

In one or more embodiments, the female connector may be selected from the group consisting of needle-free connectors, catheter luer connectors, stopcocks, and hemodialysis connectors.

In one or more embodiments, the male connector may be an intravenous tubing, stopcock end or male lock luer.

In one or more embodiments, the threads of the inner cap and the threads of the outer cap are void of interference to enable a sliding fit.

In one or more embodiments, the gaps 326 of the one or more threads 322 of the outer cap interior wall surface 320 are disposed adjacent to the grooves 324 of the outer cap interior wall surface 320 to allow sliding of the inner cap 332 against the outer cap 302.

The gaps 326 of the one or more threads 322 of the outer cap interior wall surface 320 accommodate the one or more thread-tabs 348 on the exterior wall surface 338 of the second end 344 of the inner cap 332 when the inner cap 332 slides against the outer cap 302.

In one or more embodiments, a snapping mechanism may be introduced at the rear end of inner cap 332 to lock in position with the outer cap 302 so that it can stay in place upon assembly. The mechanism has an interference such that the force resulting from screwing inner cap on male connectors can dislocate the inner cap, as well as the force resulting from pushing on the inner cap by female connector can dislocate the inner cap.

In one or more specific embodiments, the two shaft-like wings 347 on the exterior wall surface 338 of the first end 342 of the inner cap further comprise one or more pockets 349 having a snap-fit arrangement with one or more protrusions 380 disposed on the one or more grooves 324 of the outer cap interior wall surface 320 to fix the position of the inner cap 332 with the outer cap 302.

When a male luer connector is engaged to the one or more thread-tabs 348 of the exterior wall surface 338 of the second end 344 of the inner cap 332 and rotated in a clockwise direction, the one or more pockets 349 on the two shaft-like wings 347 of the inner cap 332 disengage from the one or more protrusions 380 on the outer cap interior wall surface 320 to allow the inner cap 332 to partially protrude out from the open end 310 of the outer cap 302.

When a female luer connector is engaged to the device, the inner cap 332 will be pushed and the one or more pockets 349 on the two shaft-like wings 347 of the inner cap 332 disengage from the one or more protrusions 380 on the outer cap interior wall surface 320 to allow the inner cap 332 to move toward the closed end 306 of the outer cap and into the chamber 312.

In one or more embodiments, the two shaft-like wings 347 on the exterior wall surface 338 of the first end 342 of the inner cap 332 further comprise one or more protrusions 380 having a snap-fit arrangement with one or more corresponding one or more pockets 349 disposed on the one or more grooves 324 of the outer cap interior wall surface 320 to fix the position of the inner cap 332 with the outer cap 302.

Inner cap 332 can slide back and forth with respect to outer cap 302. In one or more embodiments, the open end 310 of the outer cap 302 is situated on the same horizontal plane P as the second end 344 of the inner cap 332 in an initial state. When a male luer connector is engaged to the one or more thread-tabs 348 of the exterior wall surface 338 of the second end 344 of the inner cap 332, the inner cap 332 slides against the outer cap 302 to partially protrude out from the open end 310 of the outer cap 302. When a female luer connector is engaged to the device 300, the inner cap 332 slides against the outer cap 302 and retracts into the chamber 312 of the outer cap 302 to allow the female luer connector to engage the one or more threads 322 on the interior wall surface 320 of the outer cap 302. The thread-tabs 348 of the inner cap 332 and the threads 322 of the outer cap 302 are intrinsically non-interfering with each other, and are no longer restrained by interference that enables sliding fit.

Disinfecting caps currently on the market are capable of only disinfecting one of the three types of luer fitting, namely female luer of needle-free connectors, female luer of stopcocks, and male luer connectors on intravenous injection sites. Thus, to avoid having to use different types of disinfecting caps to clean different types of connectors, device 300 is self-adaptive to different types of luer connectors due to the sliding mechanism between the inner cap 332 that engages with male luer connectors and the outer cap 302 that engages with female luer connectors thereby allowing the user to clean different types of connectors with a single device. Thus, to avoid having to use different types of disinfecting caps to clean different types of connectors, device 300 and other embodiments of the present disclosure provides a single device to be used for cleaning different types of connectors. Upon mounting the outer cap 302 onto female luer connectors, the inner cap 332 retreats towards the chamber 312 at the closed end 306 of the outer cap 302, thus, providing space for female luer connectors to be inserted and screwed onto the threads 322 of the outer cap. Upon mounting the inner cap of device 300 onto a male luer connector, the one or more thread-tabs 348 on the exterior wall surface 338 of the second end 344 of the inner cap 332 engage with the threads on the male luer connector. Hence the disclosed cap can be mounted onto both male and female luers. The threads of the inner cap and the threads of the outer cap are intrinsically non-interfering with each other and the dimension of the threads of the inner cap and the threads of the outer cap are independent with each other while meeting the luer standard.

The device 300 can achieve disinfection when used on luer connectors by integrating an absorbent material having a disinfectant or antimicrobial agent in the chamber 312 of the outer cap 302. The disinfectant or antimicrobial agent can be directly included in the chamber or disinfectant or antimicrobial agent can be absorbed into sponges or foam material that fills the chamber of outer cap. In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In one or more embodiments, the disinfectant or antimicrobial agent may be a fluid or a gel. In one or more embodiments, the absorbent material compresses toward the closed end of the chamber upon connection to the female luer connector or the male luer connector. The compression of the absorbent material disinfects the female luer connector or the male luer connector.

The peelable seal on the end face 316 to prevent the disinfectant or the antimicrobial agent from exiting the chamber 312.

In one or more embodiments, the outer cap exterior wall surface 318 includes a plurality of grip members.

Figure 25:
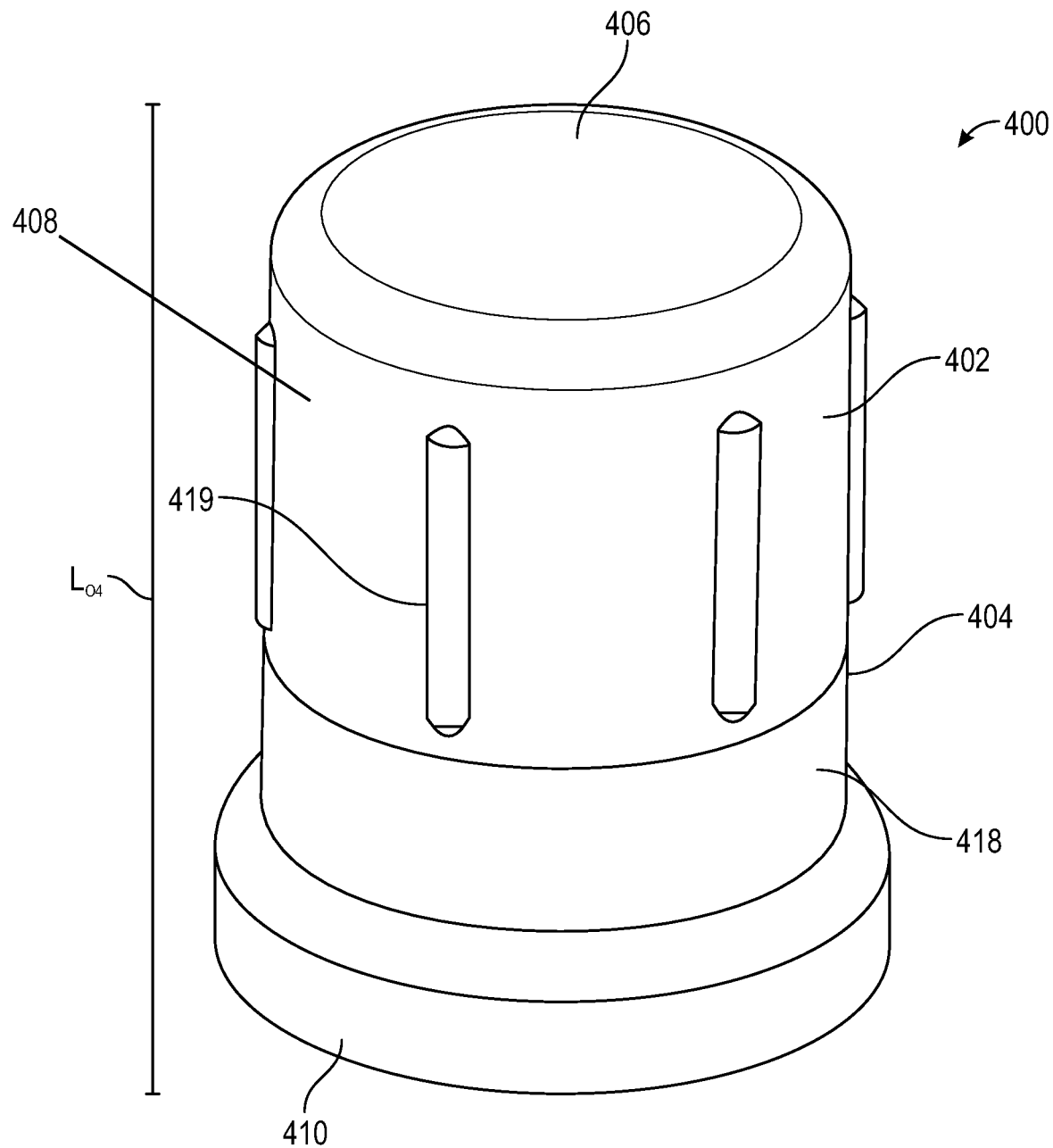
FIG. 25 shows a perspective view of a device according to a fourth embodiment.
Figure 27:
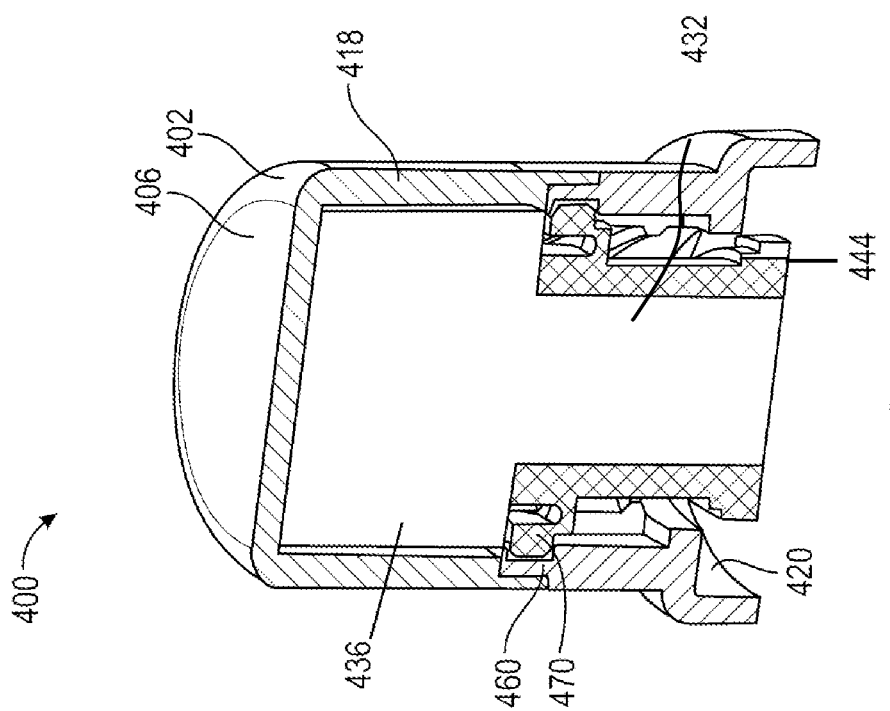
FIG. 27 shows a cross-sectional view of a device according to a fourth embodiment.
Figure 26:
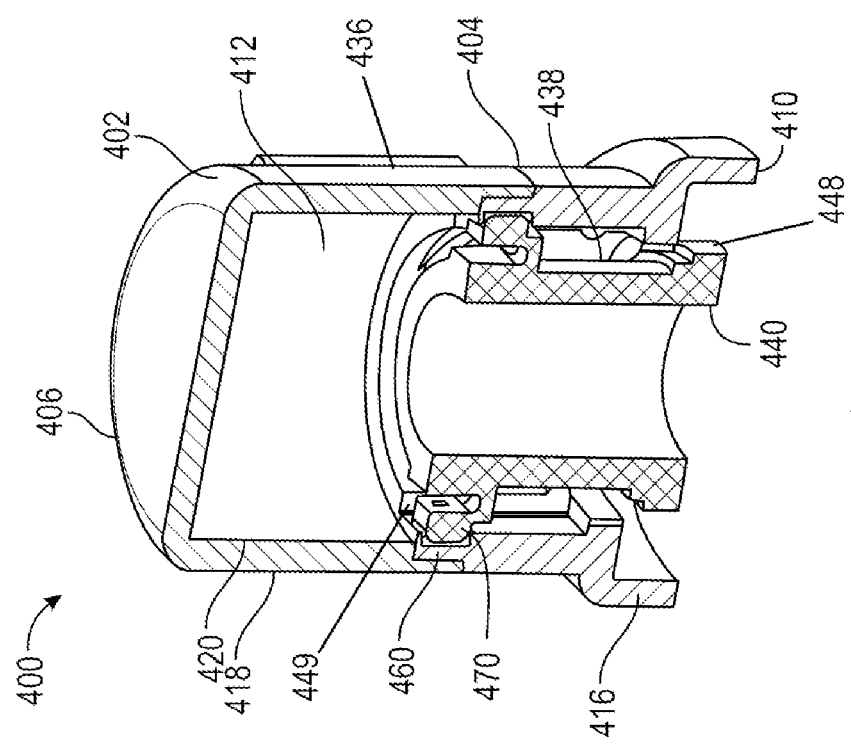
FIG. 26 shows a cross-sectional view of a device according to a fourth embodiment.
Figure 28:
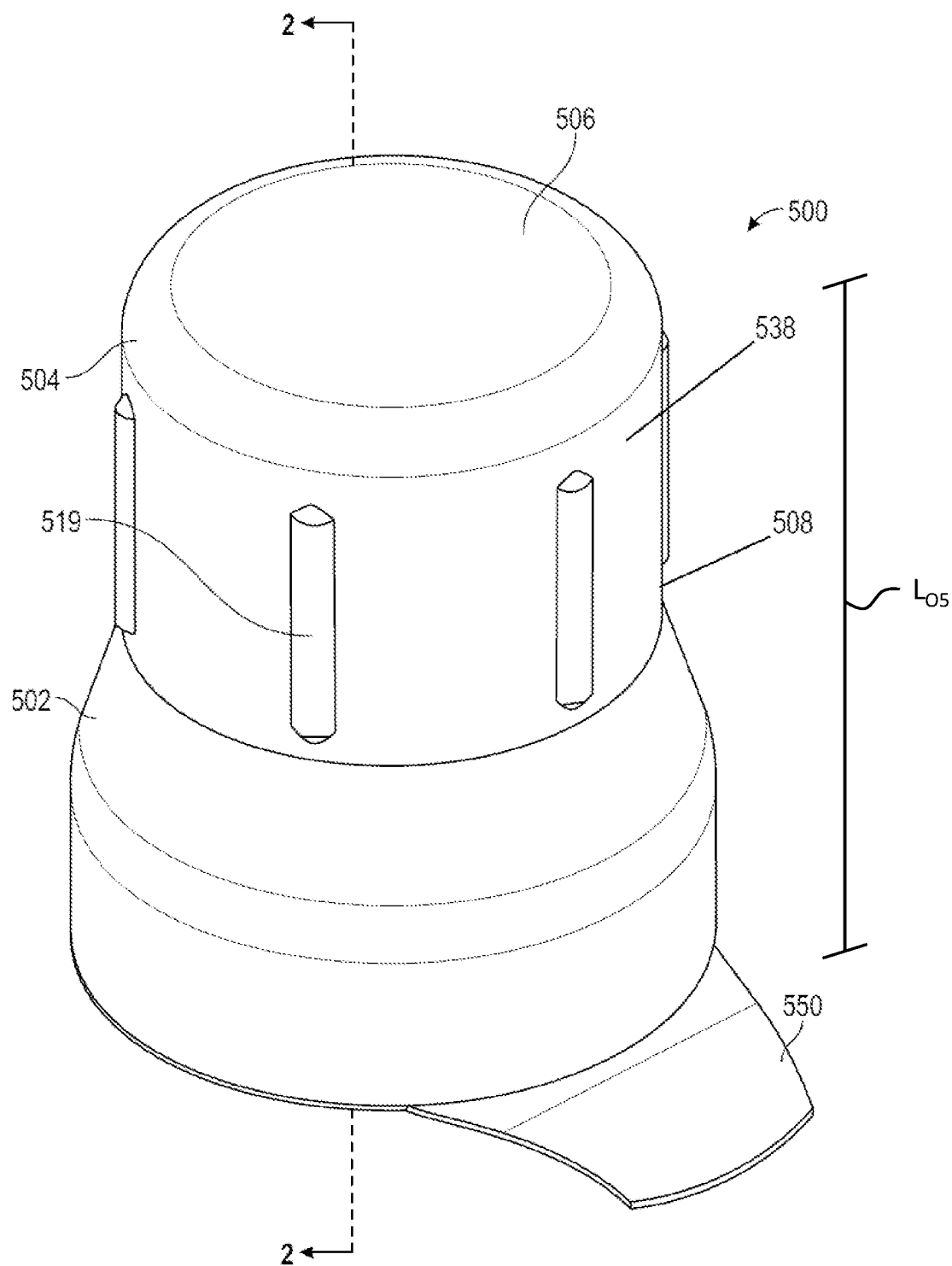
FIG. 28 shows a perspective view of a device according to a fifth embodiment.
Figure 30:
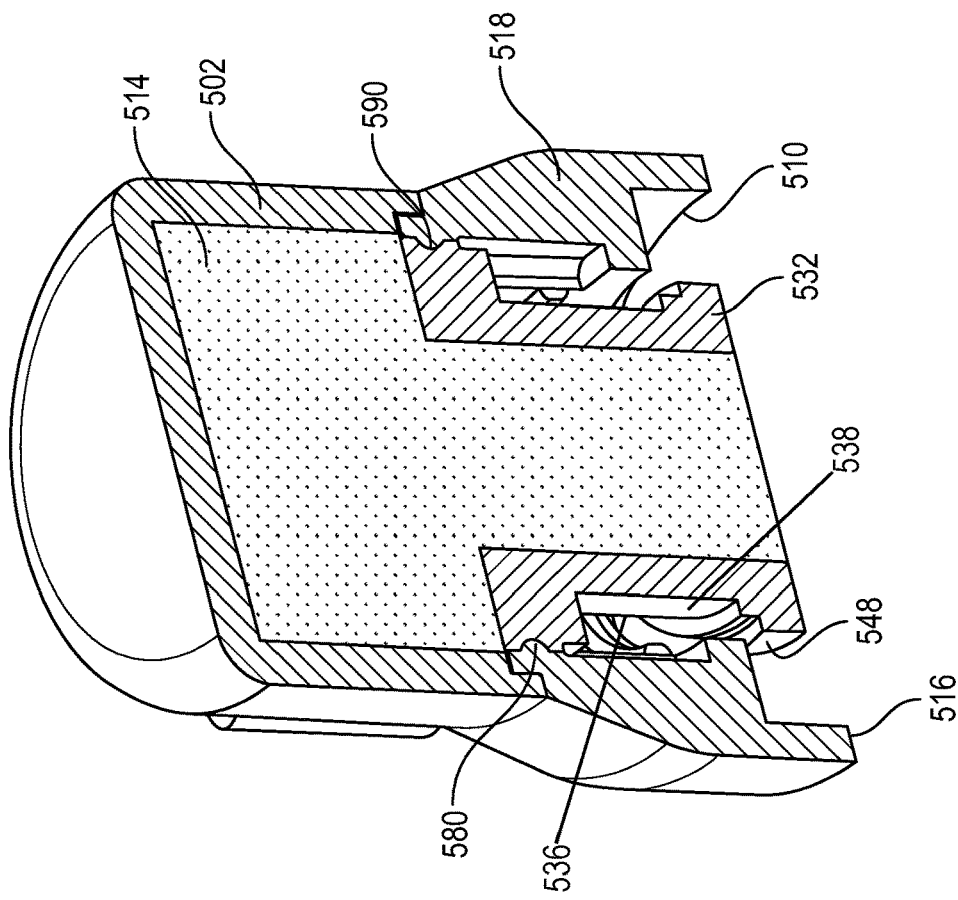
FIG. 30 shows a cross-sectional view of a device with an absorbent material according to a fifth embodiment.
Figure 29:
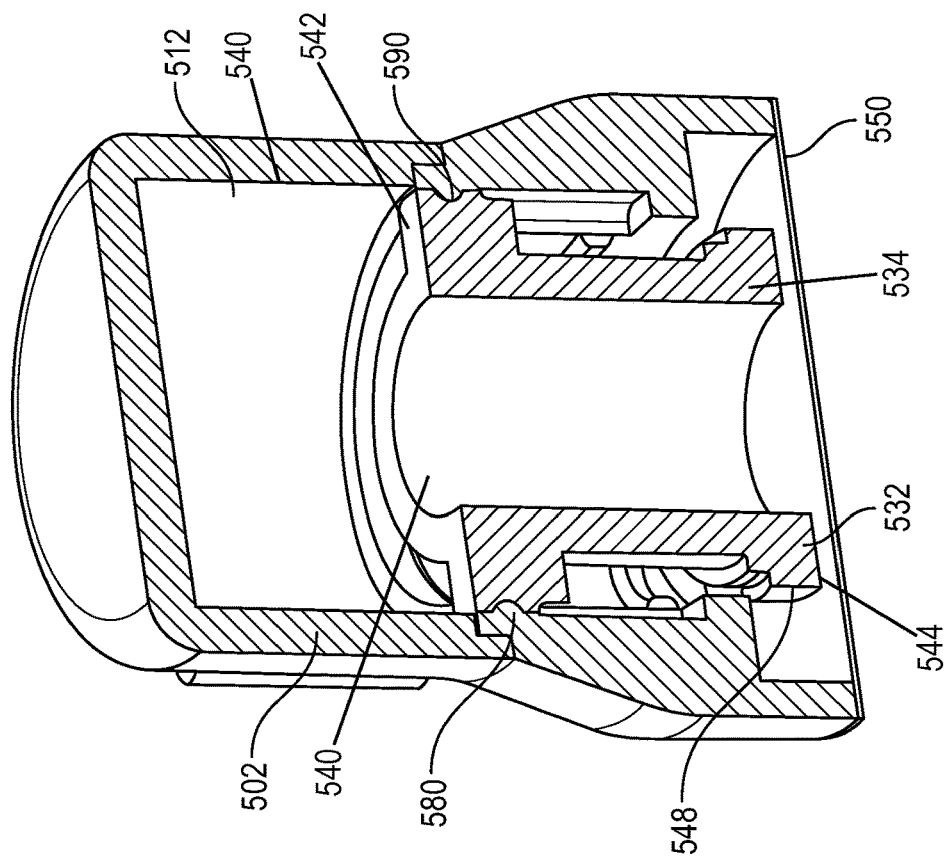
FIG. 29 shows a cross-sectional view of a device according to a fifth embodiment.

Referring to FIGS. 25-27, a device 400 for connection to a medical connector according to a fourth exemplary embodiment of the present disclosure generally comprises an outer cap 402, an inner cap 432, and a peelable seal.

The outer cap 402 comprises an integral body 404, a closed end 406, an outer cap annular wall 408 having a length $L_{O4}$ extending from the closed end 406 to an open end 410 and defining a chamber 412 containing an absorbent material and disinfectant or antimicrobial agent. The open end 410 of the outer cap 402 defines an end face 416.

The outer cap annular wall 408 comprises an outer cap exterior wall surface 418 and an outer cap interior wall surface 420. The outer cap interior wall surface 420 includes one or more pockets 460.

The inner cap 432 comprises an integral body 404 having an annular wall 436 having an exterior wall surface 438 and an interior wall surface 440 with a first end 442 of the inner cap facing the closed end of the outer cap, a second end 444 of the inner cap facing the open end of the outer cap. The exterior wall surface of the first end of the inner cap includes a flexure hinge 470 adapted to engage the one or more pockets 460 of the outer cap interior wall surface 420 to fix the position of the inner cap 432 with the outer cap 402. The exterior wall surface 438 of the second end 444 of the inner cap 432 includes one or more thread-tabs 448 adapted to engage a male luer connector.

In one or more embodiments, the inner cap 432 is connected to the interior surface 420 of the outer cap by an elastic element designed as a flexure hinge 470, as shown in FIG. 26. The flexure hinge is a relatively long cantilever hinge connected to the inner cap. The hinge assembly further includes two flexures that are provided to secure the inner cap 432 with the outer cap 402. Each flexure includes a first portion that is connected to the inner cap, a second portion that is connected to one or more pockets 449 formed in the interior surface 420 of the annular wall of the outer cap 402. As used herein, a flexure hinge 470 is a hinge that allows motion by bending a load element. In one embodiment, the flexure hinge 470 is fabricated from any suitable plastic material that enables the movement of the inner cap 432 with respect to the outer cap 402. In one or more embodiments, the flexure hinge 470 is fabricated from material that can be repeatedly flexed without degradation or failure.

In one or more embodiments, flexure hinge 470 may be made from a plastic material preferably such as injection molded polypropylene or ultra-high molecular weight polyethylene (UHMW-PE) whose material properties permit a short flexure length while at the same time permitting a high number of flexing motion cycles.

The peelable seal on the end face 416 to prevent the disinfectant or the antimicrobial agent from exiting the chamber 412.

In one or more embodiments, the open end 410 of the outer cap 402 is situated on a same horizontal plane as the second end 444 of the inner cap 432 in an initial state.

When a male luer connector is engaged to the one or more thread-tabs 448 of the exterior wall surface 438 of the second end 444 of the inner cap 432 and the connector is rotated in a clockwise direction when viewed from the open end of the cap, the flexure hinge 470 on the inner cap disengages from the pocket 449 on the outer cap interior wall surface 420 to allow the inner cap 432 to partially protrude out from the open end 410 of the outer cap 402. When a male luer connector is engaged to the one or more thread-tabs 448 of the exterior wall surface 438 of the second end 444 of the inner cap 432 and rotated in a counter-clockwise direction, the inner cap 432 retracts into the chamber 412 of the outer cap 402.

When a female luer connector is engaged to the device, the inner cap 432 will be pushed and the interlocking between the flexure hinge 470 on the inner cap and the pocket 449 on the outer cap will be dislodged to allow the inner cap 432 to move toward the closed end 406 of the outer cap and into the chamber 412.

The inner cap 432 and/or the outer cap 402 is made from any of a number of types of plastic materials such as polycarbonate, polypropylene, polyethylene, glycol-modified polyethylene terephthalate, acrylonitrile butadiene styrene or any other moldable plastic material used in medical devices.

In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

In one or more embodiments, the outer cap exterior wall surface 418 includes a plurality of grip members 419.

In one or more embodiments, the female luer connector may be selected from a group consisting of needle-free connectors, stopcocks, and hemodialysis connectors.

In one or more embodiments, the male luer connector may be an intravenous tubing end, stopcock or male lock luer.

Referring to FIGS. 28-34, a device 500 for connection to a medical connector according to a fifth exemplary embodiment of the present disclosure generally comprises an outer cap, an inner cap, and a peelable seal.

The outer cap 502 comprises an integral body 504, a closed end 506, an annular wall 508 having a length $L_{O5}$ extending from the closed end 506 to an open end 510 and defining a chamber 512 containing an absorbent material 514 and disinfectant or antimicrobial agent. The open end of the body defines an end face 516. In one or more embodiments, the annular wall comprises a flared curvature at the open end of the body defining an end face 516. In one or more embodiments, the integral body 504 of the outer cap has a geometry that is modified to reduce the outer diameter and height of the outer cap. The reduction in size and weight reduces the risk of interfering with patients' activity and irritation on patients' skin. Luer threads on the inner cap are designed to not interfere with the threads on the outer cap without additional cuts into the outer cap threads, thus facilitate the molding process.

The outer cap annular wall 508 comprises an outer cap exterior wall surface 538 and an outer cap interior wall surface 540, the interior wall surface 540 having one or more protrusions 580. The inner cap 532 comprises an integral body 534 having an annular wall 536 having an exterior wall surface 538 and an interior wall surface 540 with a first end 542 of the inner cap facing the closed end of the outer cap, a second end 544 of the inner cap facing the open end of the outer cap. The exterior wall surface of the first end of the inner cap includes a dimple 590 adapted to engage the one or more protrusions of the interior wall surface of the outer cap to fix the position of the inner cap with the outer cap. The exterior wall surface of the second end of the inner cap includes one or more thread-tabs 548 adapted to engage a male luer connector. The peelable seal 550 on the end face 516 to prevent the disinfectant or the antimicrobial agent from exiting the chamber 512.

In one or more embodiments, the open end of the outer cap may be situated on a same horizontal plane as the second end of the inner cap in an initial state.

When a male luer connector is engaged to the one or more thread-tabs 548 of the exterior wall surface 538 of the second end 544 of the inner cap 532 and rotated in a clockwise direction, the inner cap 532 partially protrude out from the open end 510 of the outer cap 502.

When a male luer connector is engaged to the one or more thread-tabs 548 of the exterior wall surface of the second end of the inner cap and rotated in a counter-clockwise direction, the inner cap 532 retracts into the chamber 512 of the outer cap 502.

When a female luer connector is engaged to the device, the inner cap 532 slips and retracts into the chamber 512 of the outer cap 502.

In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

In one or more embodiments, the outer cap exterior wall surface 518 can include indicia, graphics, symbols, diagrams, words or other instructions.

In one or more embodiments, curvature is added to the outer cap exterior wall surface 518. In one or more embodiments, a plurality of gripping members 519 is added to the outer cap exterior wall surface 518 to enhance the grip. In one or more embodiments, the plurality of gripping members 519 may be in the form of ribs.

The inner cap 532 and/or the outer cap 502 is made from any of a number of types of plastic materials such as polycarbonate, polypropylene, polyethylene, glycol-modified polyethylene terephthalate, acrylonitrile butadiene styrene or any other moldable plastic material used in medical devices.

Figure 32:
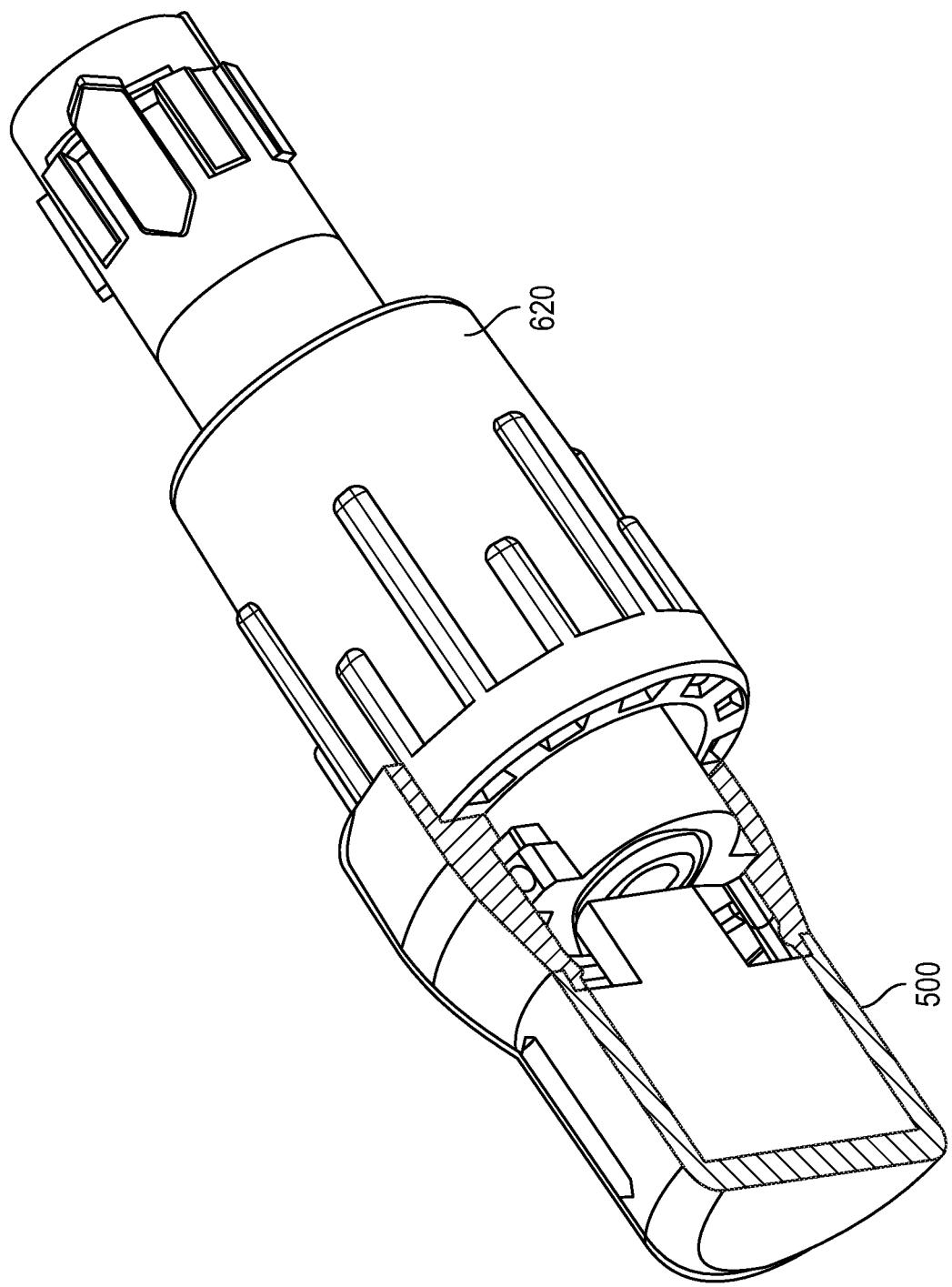
FIG. 32 shows a perspective view of a device according to a fifth embodiment in connection with a female luer connector.
Figure 35:
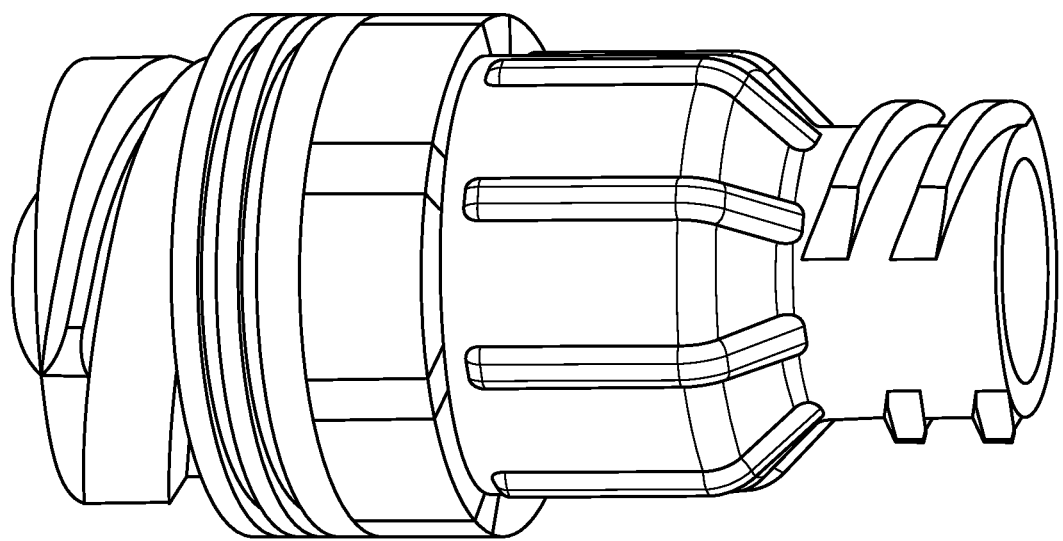
FIG. 35 shows a perspective view of a female luer connector with septum according to the prior art.
Figure 36:
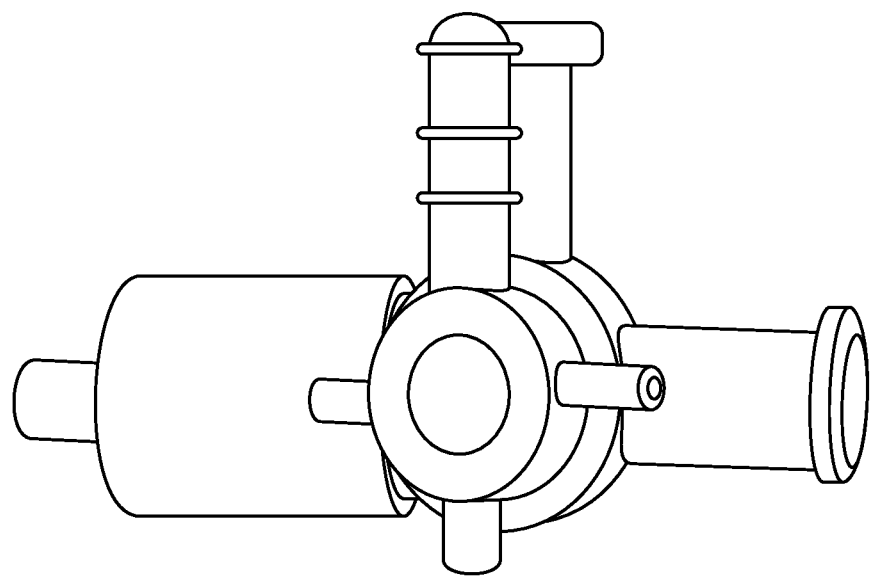
FIG. 36 shows a perspective view a female luer connector with stopcock according to the prior art.
Figure 37:
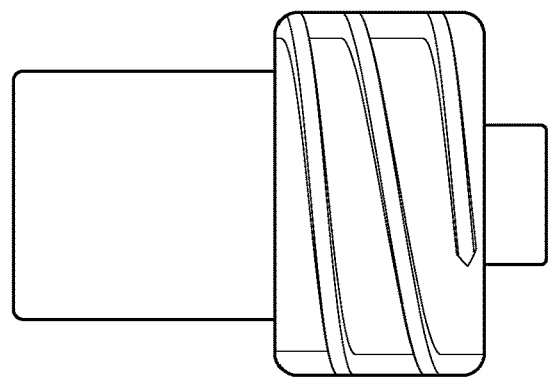
FIG. 37 shows a perspective view of a male luer connector according to the prior art.
Figure 38:
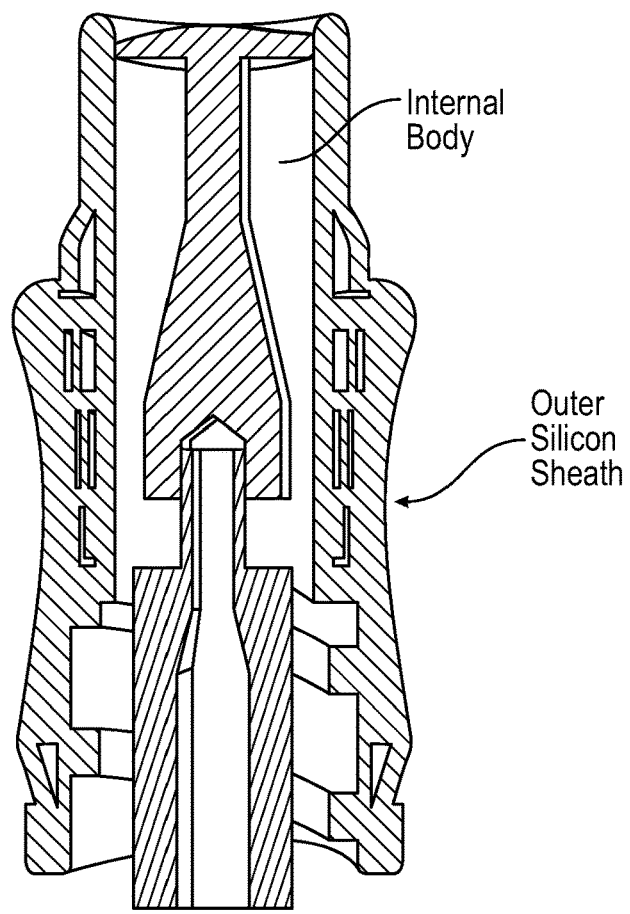
FIG. 38 shows a perspective view of a hemodialysis connector according to the prior art.

As shown in FIGS. 32 and 34, in one or more embodiments, the female connector 620 is selected from the group consisting of needle-free connectors, stopcocks, and hemodialysis connectors.

Figure 31:
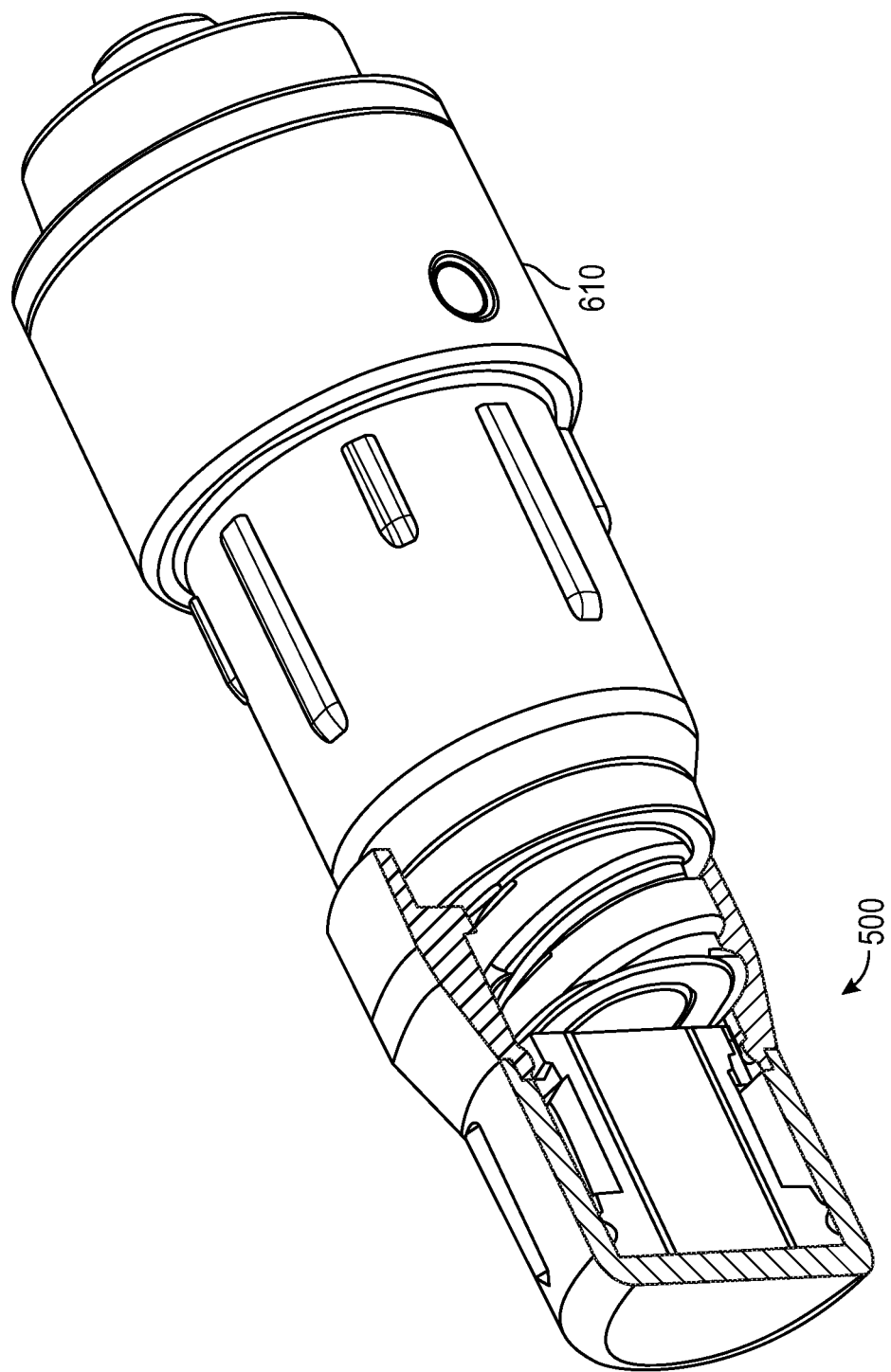
FIG. 31 shows a perspective view of a device according to a fifth embodiment in connection with a male luer connector.

As shown in FIGS. 31 and 33, in one or more embodiments, the male connector 610 may be an intravenous tubing end, stopcock or a male lock luer.

Referring to FIGS. 35 to 38, in one or more embodiments, the cap of the device of the present disclosure is tapered to form a fluid-tight seal with a male luer. In specific embodiments, the cap is compliant with ISO standards (e.g., ISO 594-1:1986 and ISO 594-2:1998) for forming a seal with a male luer.

In one or more embodiments, the cap of the device of the present disclosure has threads that have a size and pitch to engage a threadable segment of a female connector, such as for example, a female luer connector. Such connectors are generally and commonly used as catheter and other fluid-tight protective connectors in medical applications. In some embodiments, the cap provides a protective cover for a female luer connector when engaged with the connector when threads from the female luer connector engage and form a releasable connection with threads of the cap.

In some embodiments, the connector comprises a needleless injection site, which may sometimes be referred to as a needleless injection port, hub, valve, or device, or as a needleless access site, port, hub, valve, or device, and which can include such brands as, for example, Clave® (available from ICU Medical, Inc.), SmartSite® (available from Cardinal Health, Inc.), and Q-Syte™ (available from Becton, Dickinson and Company). In some embodiments, the cap can be connected with any of a variety of different needleless injection sites, such as those previously listed. In one or more embodiments, after the cap has been coupled with connector, it is unnecessary to disinfect (e.g. treat with an alcohol swab) the connector prior to each reconnection of the connector with another connector, as the connector will be kept in an uncontaminated state while coupled with the cap. Use of the cap replaces the standard swabbing protocol for cleaning connectors.

In one or more embodiments, threads of the cap are sized and pitched to engage threads of a male luer-lock connector. For example, connector can comprise the end of an IV tubing set that is disconnected from an IV catheter needleless injection site.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A device for connection to a medical connector, the device comprising:
    an outer cap comprising an integral body, a closed end, an outer cap annular wall having a length $L_{O1}$ extending from the closed end to an open end and defining a chamber containing an absorbent material and disinfectant or antimicrobial agent, the open end defining an end face;
    the outer cap annular wall having an outer cap exterior wall surface and an outer cap interior wall surface, the outer cap interior wall surface having one or more threads;
    an inner cap comprising an integral body having an inner cap annular wall having an exterior wall surface and an interior wall surface with a first end of the inner cap facing the closed end of the outer cap, wherein the inner cap annular wall having an inner cap length $L_{I1}$ extending from the first end to a second end of the inner cap and being less than the length $L_{O1}$ of the outer cap; the second end of the inner cap facing the open end of the outer cap, the exterior wall surface of the first end of the inner cap having one or more threads to engage with the threads on the interior wall surface of the outer cap, the exterior wall surface of the second end of the inner cap having one or more threads adapted to engage a male luer connector; and
    a peelable seal on the end face to prevent the disinfectant or the antimicrobial agent from exiting the chamber.

2. The device of claim 1, wherein the one or more threads on the interior wall surface of the outer cap having threads adapted to engage a female luer connector.

3. The device of claim 2, wherein a compression of the absorbent material toward the closed end of the chamber occurs upon connection to the female luer connector or the male luer connector.

4. The device of claim 3, wherein the compression of the absorbent material disinfects the female luer connector or the male luer connector.

5. The device of claim 1, wherein the open end of the outer cap is situated on approximately a same horizontal plane P as the second end of the inner cap in an initial state.

6. The device of claim 1, wherein when a male luer connector is engaged to the one or more threads of the exterior wall surface of the second end of the inner cap and rotated in a clockwise direction, the inner cap partially protrudes out from the open end of the outer cap.

7. The device of claim 1, wherein when a male luer connector is engaged to the one or more threads of the exterior wall surface of the second end of the inner cap and rotated in a counter-clockwise direction, the inner cap retracts into the chamber of the outer cap.

8. The device of claim 1, wherein when a female luer connector is engaged to the device, the inner cap slips and retracts into the chamber of the outer cap.

9. The device of claim 1, wherein the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

10. The device of claim 1, wherein the disinfectant or antimicrobial agent is a fluid or a gel.

11. The device of claim 1, wherein the outer cap exterior wall surface includes a plurality of grip members.

12. The device of claim 1, wherein a female luer connector is selected from the group consisting essentially of needle-free connectors, stopcocks, and hemodialysis connectors.

13. The device of claim 1, wherein the male connector is an intravenous tubing end or stopcock.

14. The device of claim 1, wherein the peelable seal comprises an aluminum or multi-layer polymer film peel back top.

* * * * *

UNITED STATES PATENT AND TRADEMARK OFFICE
CERTIFICATE OF CORRECTION

| | | |
|---|---|---|
| PATENT NO. | : 11,273,298 B2 | Page 1 of 1 |
| APPLICATION NO. | : 16/378015 | |
| DATED | : March 15, 2022 | |
| INVENTOR(S) | : Nicholas Erekovcanski et al. | |

It is certified that error appears in the above-identified patent and that said Letters Patent is hereby corrected as shown below:

On the Title Page

• Page 2, Item (56), Column 1, under "References Cited – U.S. Patent Documents", Line 30, replace "2010/0004020" with "2010/0000040".

In the Specification

• Column 11, Line 29, replace "release ably" with "releasably".

Signed and Sealed this
Seventh Day of June, 2022

Katherine Kelly Vidal
*Director of the United States Patent and Trademark Office*